(12) United States Patent
Blumenfeld et al.

(10) Patent No.: US 6,733,729 B2
(45) Date of Patent: May 11, 2004

(54) APPARATUS FOR GENERATING A TEMPERATURE GRADIENT AND METHODS FOR USING THE GRADIENT TO CHARACTERIZE MOLECULAR INTERACTIONS

(75) Inventors: Martin Blumenfeld, Minneapolis, MN (US); Mark Fisher, Burnsville, MN (US); Fred Williamson, Minneapolis, MN (US); Gregory T. Cibuzar, Eagan, MN (US); Brian G. Van Ness, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/853,806

(22) Filed: May 11, 2001

(65) Prior Publication Data

US 2002/0015995 A1 Feb. 7, 2002

Related U.S. Application Data

(62) Division of application No. 09/630,172, filed on Aug. 1, 2000, now Pat. No. 6,544,477.

(51) Int. Cl.[7] .......................... G01N 21/01; G01N 15/06; G01N 33/53; C12Q 1/68; C12M 1/34
(52) U.S. Cl. ...................... 422/82.12; 422/68.1; 435/6; 435/7.1; 435/287.1; 435/287.2
(58) Field of Search .................. 435/6, 91.1, 283.1, 435/287.1, 287.2; 422/68.1, 50, 82.12; 257/714, 715; 438/106, 121

(56) References Cited

U.S. PATENT DOCUMENTS

| | | |
|---|---|---|
| 3,742,192 A | 6/1973 | Brzuszek et al. |
| 4,422,129 A | 12/1983 | Briant et al. |
| 4,654,624 A | 3/1987 | Hagan et al. |
| 4,953,387 A | 9/1990 | Johnson et al. |
| 5,066,377 A | 11/1991 | Rosenbaum et al. |
| 5,198,382 A | 3/1993 | Campbell et al. |
| 5,255,976 A | 10/1993 | Connelly |
| 5,293,563 A | 3/1994 | Ohta .......................... 365/190 |
| 5,459,325 A | 10/1995 | Hueton et al. ............ 250/458.1 |
| 5,552,322 A | 9/1996 | Nemoto et al. ........... 435/287.2 |
| 5,552,928 A | 9/1996 | Furuhashi et al. .......... 359/379 |
| 5,556,539 A | 9/1996 | Mita et al. ................ 210/195.2 |
| 5,578,832 A | 11/1996 | Trulson et al. ............ 250/458.1 |
| 5,631,734 A | 5/1997 | Stern et al. .................. 356/317 |

(List continued on next page.)

FOREIGN PATENT DOCUMENTS

| | | |
|---|---|---|
| EP | 0 890 651 A1 | 1/1999 |
| EP | 1 108 472 A2 | 6/2001 |
| EP | 1 123 739 A1 | 8/2001 |

OTHER PUBLICATIONS

Peterson et al., Experimental investigation of micro heat pipes fabricated in silicon wafers. Journal of Heat Transfer, 115, 751–756, 1993.*
Jiang et al., "A Micro–Channel Heat Sink with Integrated Temperature Sensors for Phase Transition Study," *12th IEEE International Conference,* Orlando, FL, 1999, pp. 159–164.
Jiang et al., "Unsteady characteristics of a thermal microsystem," *Sensors and Actuators,* 2000, 82:108–113.

*Primary Examiner*—Ethan Whisenant
*Assistant Examiner*—Frank W Lu
(74) *Attorney, Agent, or Firm*—Fish & Richardson, P.C. P.A.

(57) ABSTRACT

A novel apparatus for generating temperature gradients is described. The apparatus includes a semiconductive wafer and electrical connectors attached to, preferably, one of the edges of the wafer. Methods for transferring the temperature gradients to strata are described. The temperature gradients on the strata can be used for analyses of molecules, particularly biological macromolecules. The present invention also includes improved methods for determining the thermal stability of binding complexes.

19 Claims, 31 Drawing Sheets

U.S. PATENT DOCUMENTS

| | | |
|---|---|---|
| 5,632,957 A | 5/1997 | Heller et al. |
| 5,744,305 A | 4/1998 | Fodor et al. .................... 435/6 |
| 5,788,833 A | 8/1998 | Lewis et al. |
| 5,834,758 A | 11/1998 | Trulson et al. ........... 250/201.2 |
| 5,837,832 A | 11/1998 | Chee et al. ................ 536/22.1 |
| 5,871,628 A | 2/1999 | Dabiri et al. ............... 204/461 |
| 5,872,010 A | 2/1999 | Karger et al. |
| 5,874,219 A | 2/1999 | Rava et al. .................... 435/6 |
| 5,919,523 A | 7/1999 | Sundberg et al. ........... 427/333 |
| 5,925,525 A | 7/1999 | Fodor et al. .................... 435/6 |
| 5,985,356 A | 11/1999 | Schultz et al. |
| 5,985,555 A | 11/1999 | Bertling |
| 6,023,961 A | 2/2000 | Discenzo et al. |
| 6,074,868 A | 6/2000 | Blumenfeld ............. 435/286.1 |
| 6,346,383 B1 | 2/2002 | Kajiyama et al. |
| 6,428,749 B1 * | 8/2002 | Kajiyama et al. .......... 422/68.1 |

* cited by examiner

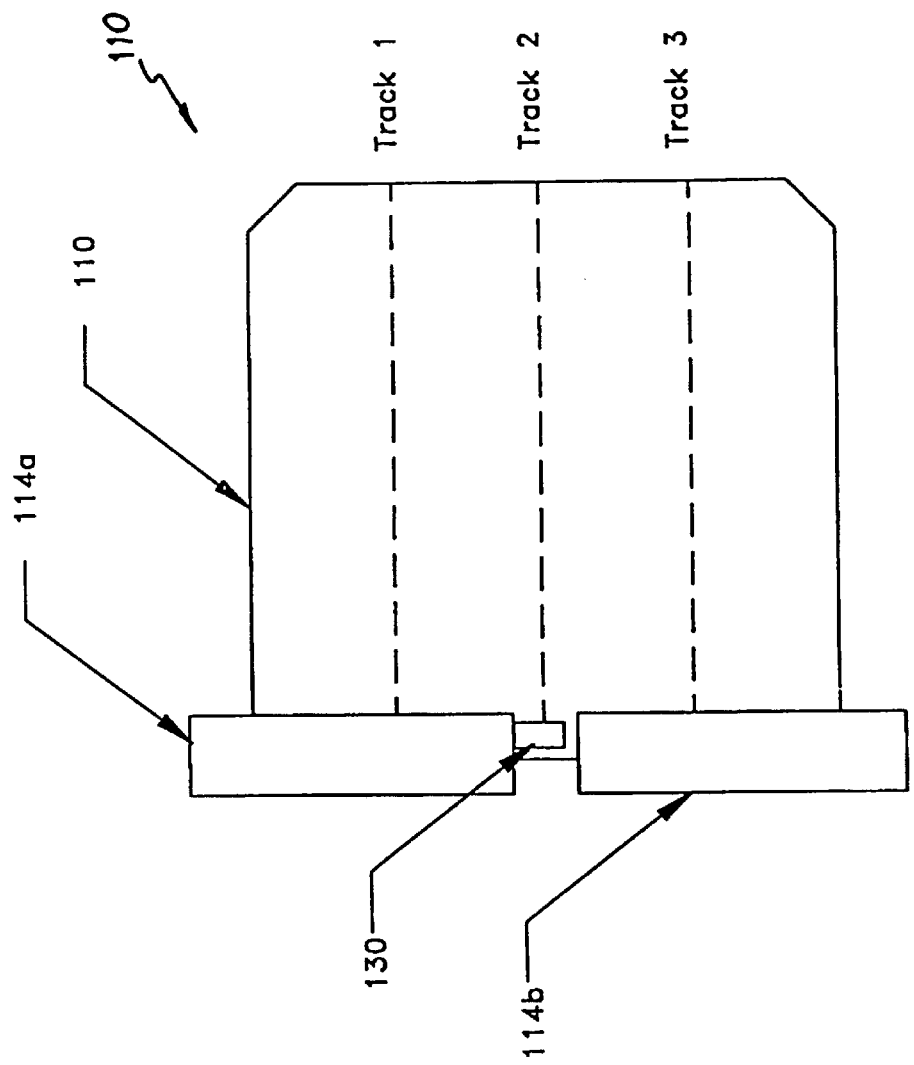

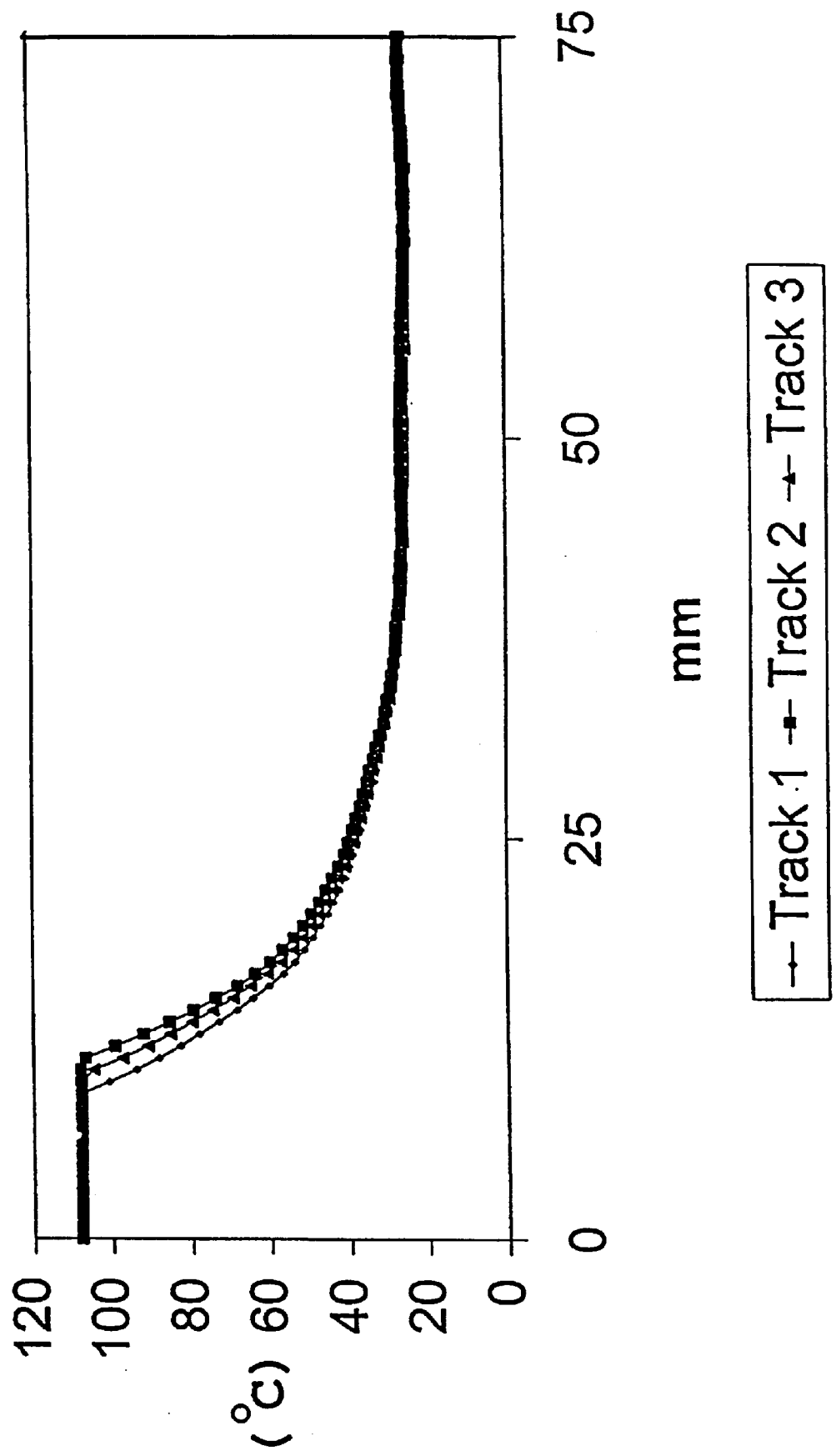

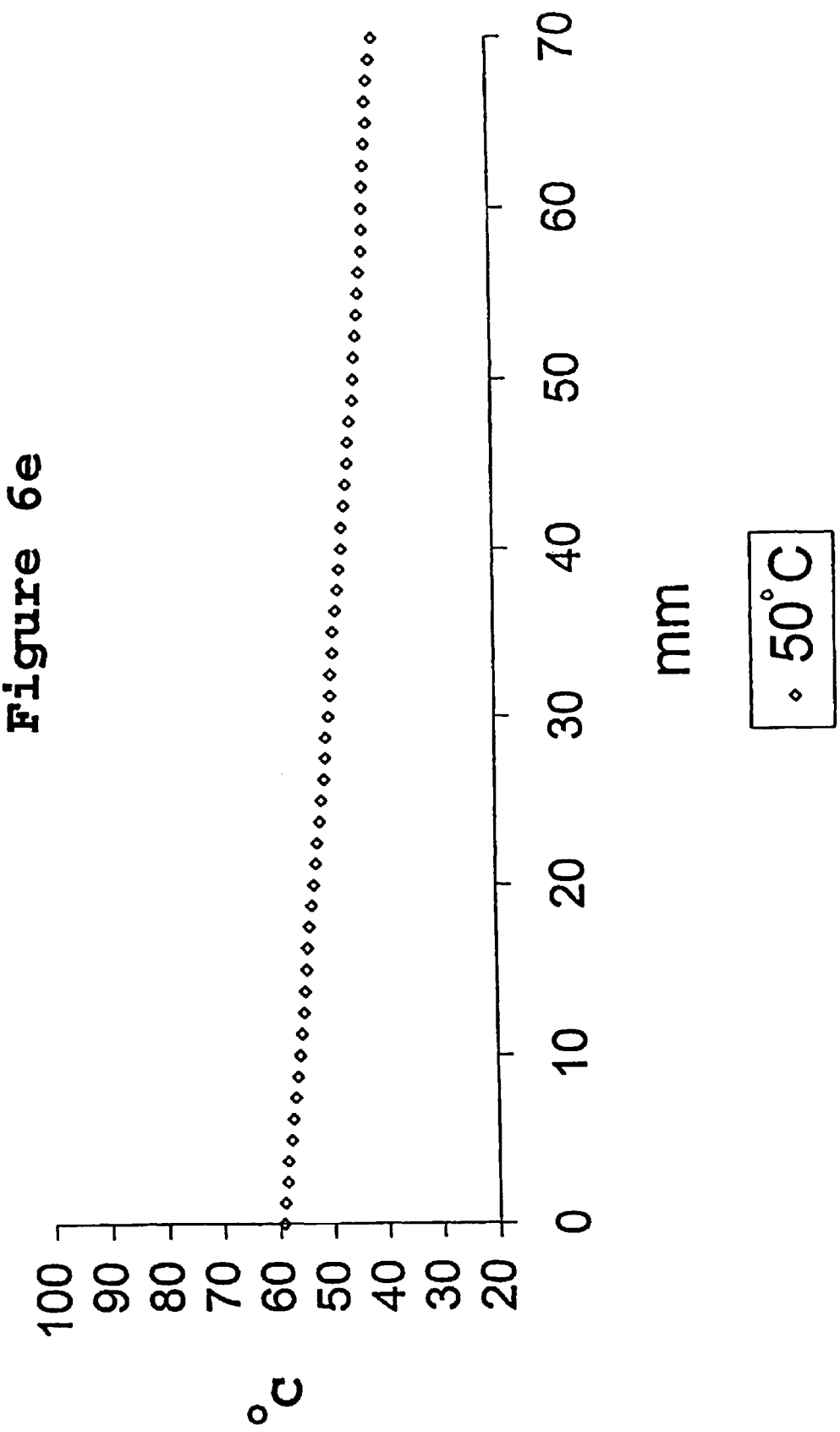

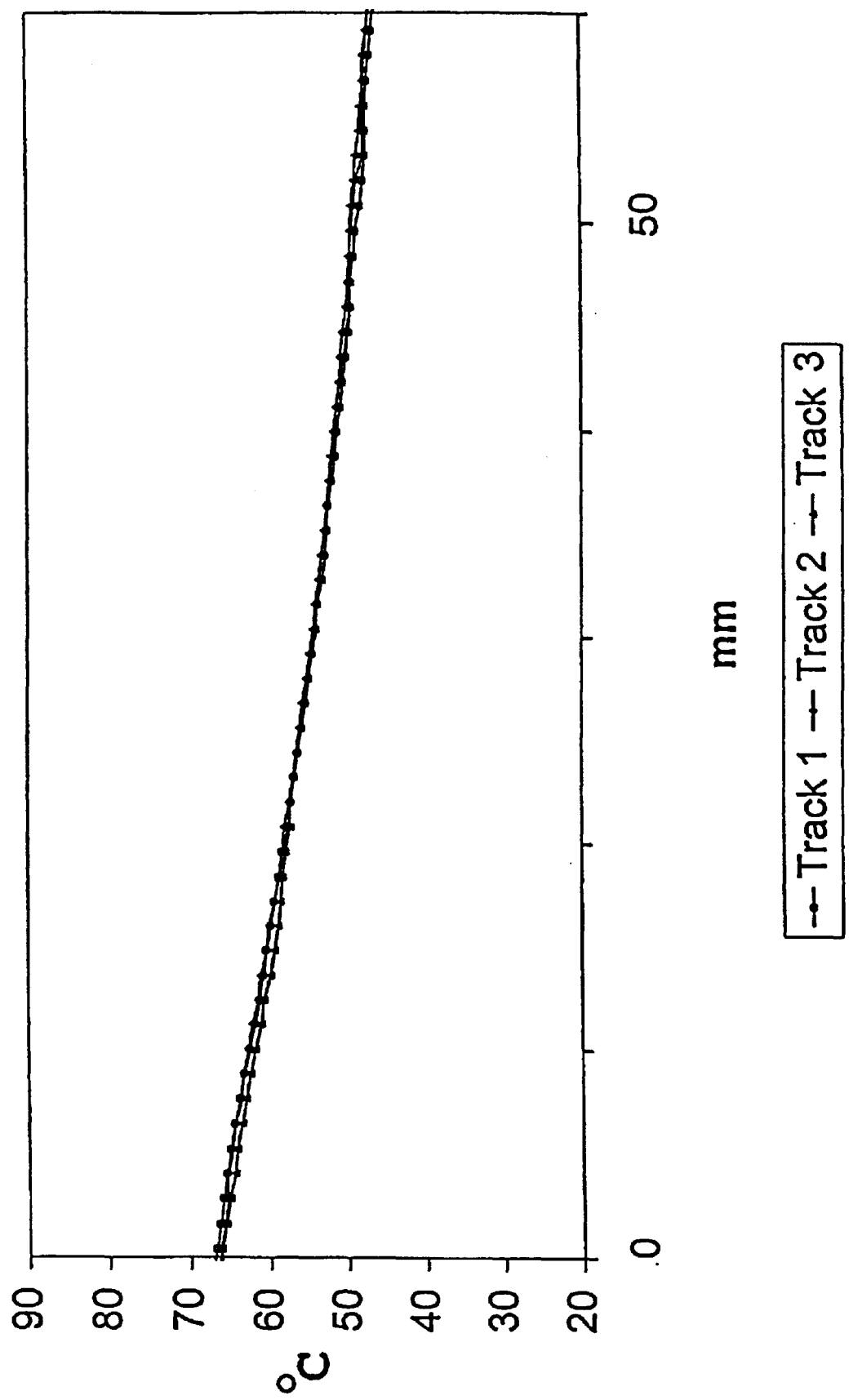

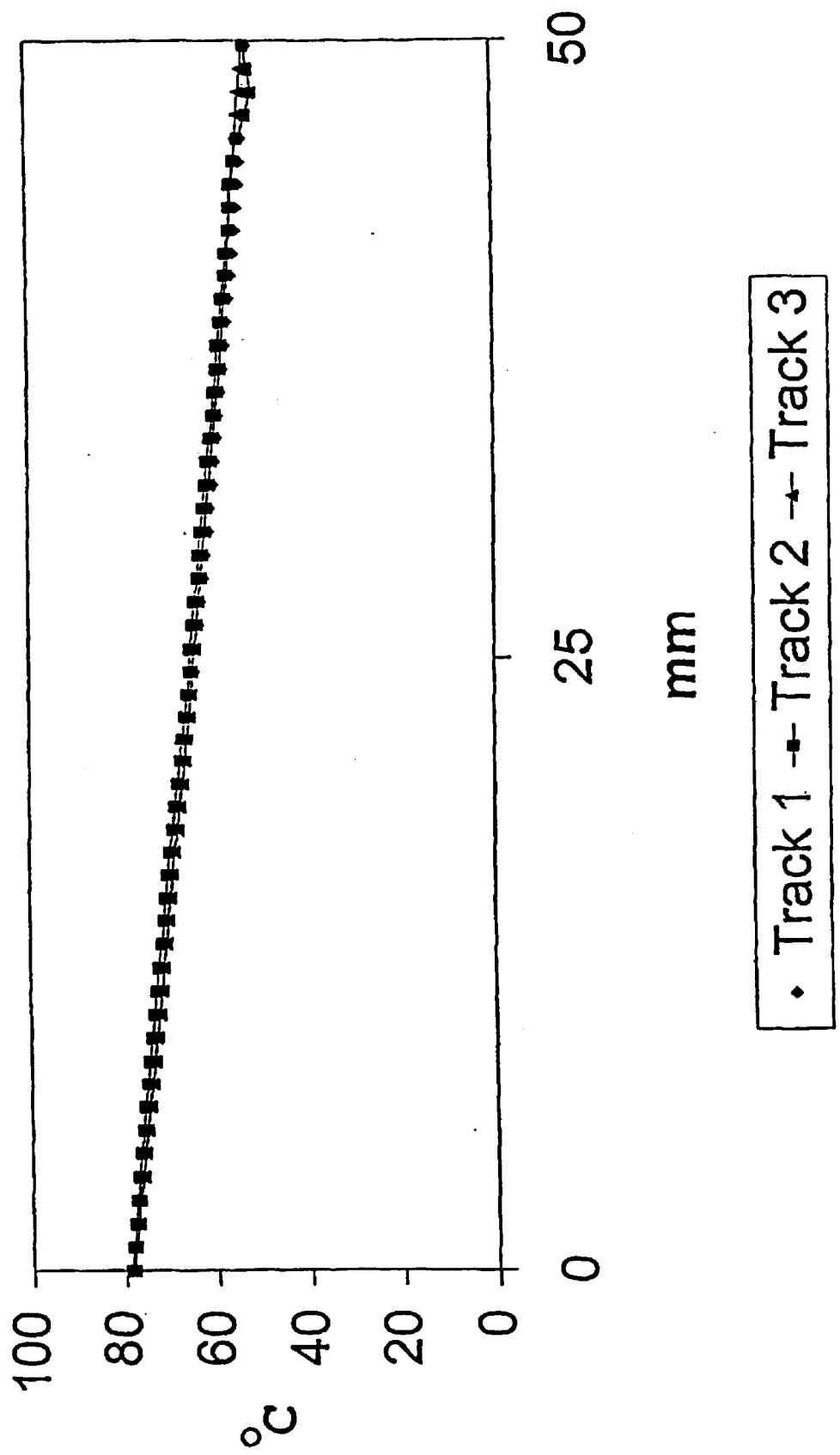

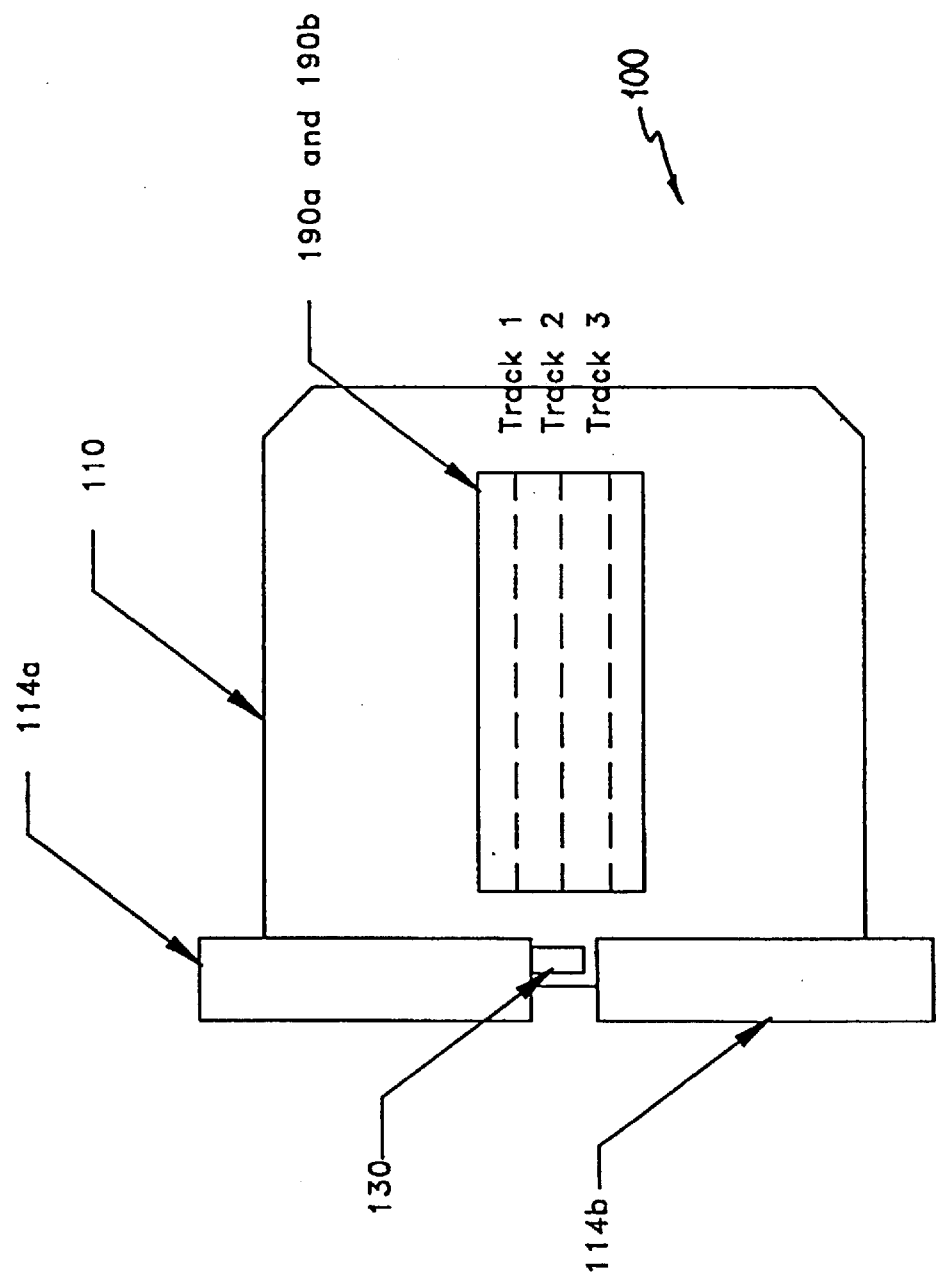

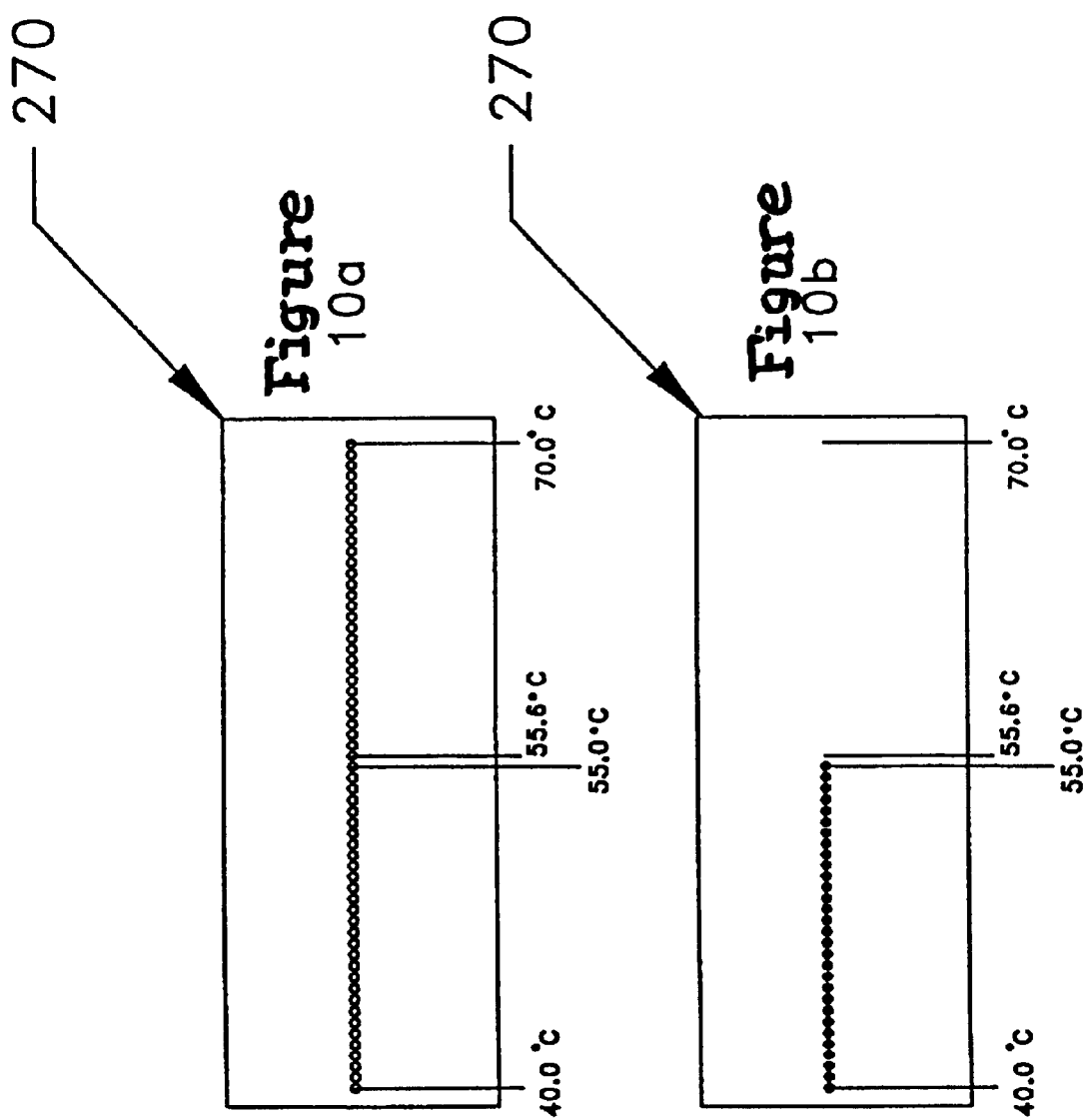

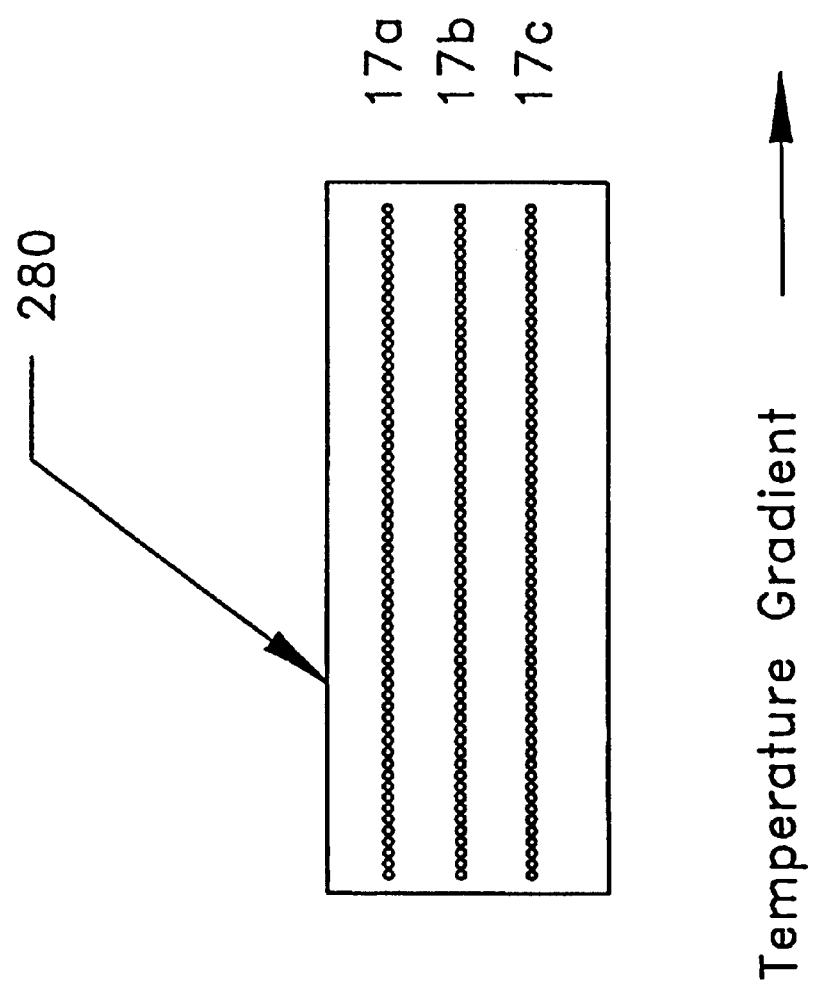

APPARATUS FOR GENERATING A TEMPERATURE GRADIENT AND METHODS FOR USING THE GRADIENT TO CHARACTERIZE MOLECULAR INTERACTIONS

CROSS REFERENCE TO RELATED APPLICATIONS

This application is a divisional of and commonly assigned U.S. patent application Ser. No. 09/630,172, filed Aug. 1, 2000 now U.S. Pat. No. 6, 544, 477 to Blumenfeld et al., entitled *APPARATUS FOR GENERATING A TEMPERATURE GRAIENT AND METHODS FOR USING THE GRADIENT TO CHARACTERIZE MOLECULAR INTERACTIONS*," incorporated herein be reference.

BACKGROUND OF THE INVENTION

This invention relates to an apparatus that generates a thermal gradient, particularly on a wafer. This invention also relates to methods of using the thermal gradient in molecular interactions, particularly for characterizing interactions involving biological macromolecules.

The stability and interactions of biological macromolecules are determined by a number of forces including, for example, ionic forces, van der Waals forces, and hydrogen bonds. Hydrogen bonds are known to be fairly weak and heat-labile forces in biological macromolecules. Small changes in the environment, in particular the temperature of the biological macromolecules, can alter the intramolecular and/or intermolecular hydrogen bonding of the macromolecules. Biological macromolecules, thus, can be sensitive to even small fluctuations in the environment.

Hybridization between nucleic acid molecules requires successful formation of hydrogen bonds between complementary nucleic acid molecules. Because hybridization relies on weak, heat-labile hydrogen bonds, hybridization is an exquisitely temperature sensitive process. Small fluctuations in the temperature and/or in the sequence of the nucleic acids can affect hybridization between complementary nucleic acid molecules.

Currently, information derived from hybridizations conducted on deoxyribonucleic acid (DNA) chips is stimulating advances in drug development, gene discovery, gene therapy, gene expression, genetic counseling and plant biotechnology. A DNA chip is a rigid flat surface, typically glass or silicon, with short chains of related nucleic acids spotted in rows and columns on it. As an example, hybridization between a fluorescently labeled single stranded nucleic acid molecule and nucleic acid molecules at specific locations on the chip can be detected and analyzed by computer-based instrumentation.

Among the technologies for creating DNA chips are photolithography, "on-chip" synthesis, piezoelectric printing and direct printing. Chip dimensions, the number of sites of DNA deposition (sometimes termed "addresses") per chip and the width of the DNA spot per "address" are dependent upon the technologies employed for deposition. The most commonly used technologies presently produce spots with diameter of 50–300 micrometers ($\mu$m). Photolithography produces spots that can have diameters as small as 1 $\mu$m. Technologies for making such chips are described, for example, in U.S. Pat. No. 5,925,525 to Fodor et al., U.S. Pat. No. 5,919,523 to Sundberg et al., U.S. Pat. No. 5,837,832 to Chee et al. and U.S. Pat. No. 5,744,305 to Fodor et al. which are incorporated herein by reference.

Hybridization to nucleic acids on DNA chips can be monitored, for example, by fluorescence optics, by radio-isotope detection, and mass spectrometry. The most widely-used method for detection of hybridization employs fluorescence-labeled DNA, and a computerized system featuring a confocal fluorescence microscope (or an epifluorescence microscope), a movable microscope stage, and DNA detection software. Technical characteristics of these microscope systems are described in U.S. Pat. No. 5,293,563 to Ohta, U.S. Pat. No. 5,459,325 to Hueton et al. and U.S. Pat. No. 5,552,928 to Furuhashi et al. which are incorporated herein by reference. Further descriptions of imaging fluorescently labeled immobilized biomolecules and analysis of the images are set forth in U.S. Pat. No. 5,874,219 to Rava et al., U.S. Pat. No. 5,871,628 to Dabiri et al., U.S. Pat. No. 5,834,758 to Trulson et al., U.S. Pat. No. 5,631,734 to Stern et al., U.S. Pat. No. 5,578,832 to Trulson et al., U.S. Pat. No. 5,552,322 to Nemoto et al. and U.S. Pat. No. 5,556,539 to Mita et al. which are incorporated herein by reference.

Currently, manipulations performed with DNA chips are limited to protocols in which all of the samples on a chip are at about the same temperature. Simple and inexpensive methods of creating temperature differentials on DNA chips would greatly expand the repertoire of procedures available that can be performed on a DNA chip.

SUMMARY OF THE INVENTION

In a first aspect, the invention pertains to an apparatus. The apparatus includes a semiconducting wafer and two electrical connectors that are adjacent to each other on the wafer. Each of the connectors are attached to the wafer at an attachment site on the wafer with a gap disposed between the two attachment sites. A power source is connected to the wafer through the two electrical connectors.

In a further aspect, the invention pertains to a method of generating a temperature gradient. The method includes attaching two electrical connectors to a semiconducting wafer, wherein each of the connectors are adjacent to each other and attached to the wafer at an attachment site with a gap disposed between the attachment sites. The method also includes connecting a power source to the wafer through the two electric connectors.

In another aspect, the invention pertains to a method of analyzing biological macromolecules. The method includes establishing a temperature gradient on a semiconducting wafer having a stratum disposed thereupon. The stratum has one or more samples that include biological macromolecules in thermal contact with the temperature gradient. The wafer has two electrical connectors connected to opposite poles of an electrical power source. The method also includes evaluating the samples to determine thermal stability of complexes formed with the biological macromolecules in the samples. The samples are evaluated by measuring a property of the sample.

In a further aspect, the invention pertains to a method of conducting nucleic acid hybridization. The method includes establishing a temperature gradient on a stratum disposed on a semiconducting wafer. One or more samples including nucleic acid molecules are disposed on the stratum that is in thermal contact with the temperature gradient. Two electrical connectors are connected to the wafer and to opposite poles of an electrical power source. The method also includes performing a hybridization protocol on the one or more samples to determine temperature effect based on the gradient.

In yet another aspect, the invention pertains to a method of assessing binding complex interactions. The method includes establishing a temperature gradient on a semiconducting wafer having a stratum disposed thereupon. The stratum has one or more samples, each sample including one or more members of a binding complex in thermal contact with the temperature gradient. The wafer has two electrical connectors connected to opposite poles of an electrical power source. The method also includes evaluating the samples to determine thermal stability of the binding complex on the stratum.

In a further aspect, the invention pertains to a method of generating a temperature gradient on a stratum. The method includes placing the stratum in thermal contact on a surface having a temperature gradient wherein the stratum has low thermal conductivity.

BRIEF DESCRIPTION OF THE DRAWINGS

FIG. 4a is a top view of the wafer of FIG. 2 with three parallel tracks used for temperature measurement.

FIG. 4b is a plot of temperature versus position on the wafer for each of the tracks indicated on the surface of the wafer in FIG. 4a.

FIG. 5c is a plot of temperature versus position for three tracks indicated in FIG. 5a using a glass microscope slide in the apparatus.

FIG. 6b is a plot of temperature versus position for each of the tracks indicated on the surface of the slide in FIG. 6a.

FIG. 6c-FIG. 6k are plots of temperature versus position for one of the tracks on the surface of the slide in FIG. 6a when the temperature controller of the apparatus was set to 40° C. 45° C., 50° C., 55° C., 60° C., 65° C., 70° C., 75° C. and 80° C., respectively.

FIG. 7b is a plot of temperature versus position for each of the tracks shown in FIG. 7a.

FIG. 8b is a detailed top view of the fluidic cell shown in FIG. 8a.

FIG. 8d is a plot of temperature versus position for each of the tracks shown in FIG. 8a.

FIG. 9a is a top view of a thermal gradient apparatus with an acrylamide gel formed between two glass slides and placed on the wafer.

FIG. 9b is a side view of the gel assembly shown in FIG. 9a.

FIG. 9c is a plot of temperature versus position for each of the tracks on the surface of the slide shown in FIG. 9a.

FIG. 10a is a diagram of a chip containing a single row of immobilized DNA spots exposed to a 40–70° C. gradient during hybridization with a complementary labeled nucleic acid probe.

FIG. 10b is a hypothetical result of the experiment depicted in FIG. 10a.

FIG. 11a is a diagram of a chip containing three different DNA molecules, each immobilized in a different row, exposed to a temperature gradient during hybridization with a labeled nucleic acid probe.

FIG. 11b is a hypothetical result of the experiment depicted in FIG. 11a.

DETAILED DESCRIPTION OF THE PREFERRED EMBODIMENTS

Figure 1:
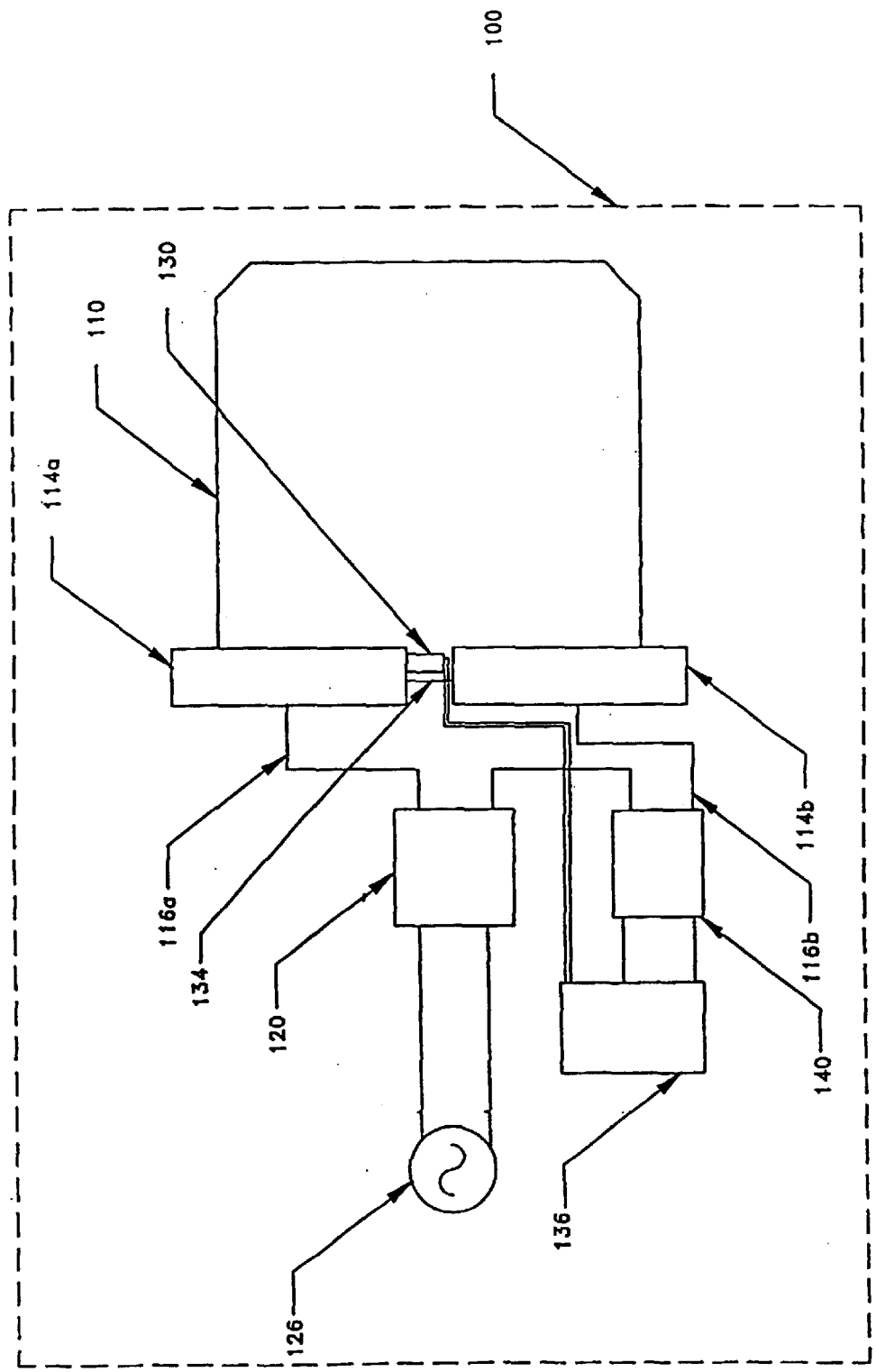
FIG. 1 is a schematic diagram of a thermal gradient apparatus.

It has been discovered that stable temperature gradients can be generated on an electrically semiconductive wafer connected to a current source. Temperature gradients are generated on the wafer, in a gradient apparatus, by applying a voltage to two physically separated sites on the wafer. The gradients are stable and approximately linear over significant distances.

It has also been discovered that a temperature gradient can be transferred onto or into an adjacent stratum when the stratum is placed in thermal contact with a surface having the temperature gradient, even if the stratum has low thermal conductivity. These temperature gradients can be used in efficient approaches for the evaluation of properties of biological macromolecules.

The gradient apparatus includes an electrically semiconductive wafer and two electrical connectors that are attached to the wafer at adjacent sites, which are referred to as the attachment sites. When the two electric connectors are connected to the opposite poles of a power source, temperature gradients can be produced on the wafer that generally are substantially perpendicular to an attachment line that is derived by connecting the attachment sites. In other words, the temperature at a given site on the wafer depends on the distance from the attachment line.

The wafer can include a proximal edge and a distal edge. The proximal edge of the wafer can include the attachment sites or can be close to the attachment sites. The side opposite the proximal edge is referred to as the distal edge of the wafer. The attachment line is derived by connecting the respective edges of the two attachment sites closest to the distal edge of the wafer. A gradient is formed approximately perpendicular to the attachment line. Away from the connectors, the temperature is approximately independent of displacements along lines parallel to the attachment line. Thus, separate tracks can be defined perpendicular to the attachment line having approximately the same temperature gradient.

Control circuitry controlling the flow of current between the wafer and the power source can provide adjustable but stable and reproducible temperature gradients. The control circuitry can include, for example, a temperature controller, a temperature sensor, a relay switch, a transformer and the like.

Small incremental changes in the temperature can be generated and advantageously detected on the surface of the wafer. The thermal gradients on the wafer generally are generated by resistive heating of the wafer and thermal conduction of the heat. In preferred embodiments, reproducible, stable temperature gradient increments of between about 0.1° C./mm and about 1.0° C./mm are generated on the semiconductive wafer. Applications of the stable temperature gradients include, but are not limited to, determination of the thermal stabilities of duplex nucleic acid molecules, polypeptide:polypeptide complexes, polypeptide:ligand complexes, polypeptide:nucleic acid complexes, polypeptide:lipid complexes, polypeptide:carbohydrate complexes and the like. As applied to nucleic acids, the ability to detect thermal sensitivity differences can provide diagnostic tools for use in a variety of applications.

The temperature gradients generated on surfaces such as a semiconductive wafer can be surprisingly transmitted to one or more stratum placed on the wafer. The stratum can include, for example, DNA chips, protein chips, glass microscopic slides, fluidic cells, liquids, acrylamide gels and the like. When the strata are placed on a wafer in a gradient apparatus of the invention, a thermal gradient can also be detected on the strata.

Analyses on a variety of biological/chemical molecules can be conducted by using the temperature gradients generated on strata. In particular, thermal stability determinations can be made using the temperature gradients on a stratum. The molecules can be linked onto or into the stratum. The molecules are generally immobilized on the stratum. By "immobilized", it is meant that the molecules are not substantially removed or substantially repositioned during subsequent washing or other experimental manipulations. Molecules can be immobilized to the stratum, for example, by covalent bonding, hydrophobic bonding, ionic bonding and absorption.

The biological/chemical molecules can include biological macromolecules, for example, nucleic acid molecules, polypeptides, carbohydrates and the like. The biological/chemical molecules can also include, for example, drugs, lipids, hormones, ligands and the like, which may or may not be macromolecules.

Cells and tissues, for example, may also be immobilized on microscopic glass slides by chemically fixing the cells onto the glass slide. Chemical fixatives can include, for example, formalin, ethanol, formaldehyde, paraformaldehyde, glutaraldehyde and the like.

The use of a gradient apparatus of the present invention with DNA chips or protein chips and various labeled probes has many diagnostic applications. In one embodiment, temperature-dependent hybridizations between single-stranded nucleic acid molecules immobilized on a chip and a labeled nucleic acid probe can be performed to form a nucleic acid duplex. Nucleic acid molecules at different positions on the chip are exposed to different temperatures based on their location relative to the temperature gradient. The hybridization signal can be correlated with the temperature. The results of these studies can establish the relatedness of similar nucleic acid molecules by estimating the number of base mismatches between each of nucleic acid molecule samples and the labeled nucleic acid probe. The gradient apparatus can be used to advantageously identify even single-base mismatches in a nucleic acid duplex.

In another embodiment, temperature dependent analyses of binding complexes can be performed on chips. The complexes can be, for example, antigen:antibody complexes, enzyme:substrate complexes, receptor:ligand complexes, polypeptide:polypeptide complexes, polypeptide:lipid complexes, polypeptide:carbohydrate complexes, polypeptide:nucleic acid complexes and the like. Binding complexes at different positions on the chip can be exposed to different temperatures based on their location relative to the temperature gradient. The results of these experiments can establish the relative dissociation strengths of related binding complexes.

A. Apparatus

The gradient apparatus of the present invention includes an electrically semiconductive wafer, a pair of electrical connectors attached to the wafer and a power source. The electrical connectors are adjacent to each other, but physically separate, when connected to the wafer. The gradient apparatus may also include control circuitry to obtain a desired temperature gradient.

The semiconductive wafer can be made from a variety of materials including, for example, germanium, silicon, gray (crystalline) tin, selenium, tellurium and boron. The semiconductive wafer is preferably made from silicon and germanium and more preferably from silicon. The semiconductive wafer preferably has a substantially uniform surface composition. The electrical conductivity of semiconductive wafers can be, for example between about $10^4$ and about $10^{-3}$ ohm$^{-1}$ cm$^{-1}$. Preferably, the electrical conductivity of semiconductive wafers is between about $10^4$ and about $10^{-2}$ ohm$^{-1}$ cm$^{-1}$.

The semiconductive wafer can be doped. Doping can increase or decrease the conductivity of the wafer. Techniques for doping are known in the art and are described, for example, in Campbell, S. A. The Science and Engineering of Microelectronic Fabrication; New York, Oxford University Press; 1996; pp. 98–102, incorporated herein by reference. Doping agents can include, for example, boron, phosphorous, arsenic and the like. Preferable semiconductive wafers are boron doped silicon wafers. Doping of a silicon wafer, for example, can change the electrical conductivity of the silicon wafer from $10^{-1}$ ohm$^{-1}$ cm$^{-1}$ to about $10^3$ ohm$^{-1}$ cm$^{-1}$.

The semiconductive wafer is preferably substantially flat and level to retain a stratum placed on the wafer for an indefinite period of time. The wafer, preferably, is also smooth to optimize efficient conductive heat transfer to the stratum.

In some preferred embodiments, the wafer can include a plurality of edges, preferably four edges. The wafer may be in the shape of a polygon, for example, a pentagon, a hexagon and the like. The wafer may also be curvilinear. The wafer can be substantially shaped, for example, as a rectangle, a square or other parallelograms. The wafer edges may have corresponding substantially rectangular edges, square edges and the like. The corners, for example, may be 90° corners, clipped corners and the like. Alternatively, the wafer may have rounded corners and thus, can include, for example, ovoid wafers, rectangular-like wafer with rounded corners. Wafers with rounded corners may not have corners that clearly delineate the different edges. In these embodiments, a rectangle with corresponding edges can be drawn over the edge of the wafer to approximate the shape of the wafer. This approximate rectangle can be used to describe the gradient and relative points on the wafer surface. All of these wafers, however, can be used in the gradient apparatus described herein.

Two electrical connectors are generally attached to the wafer adjacent to each other but physically separated. By adjacent, it is meant that the two electrical connectors are approximately at the same edge but are not in physical contact with each other. Preferably, the electrical connectors are attached to the same edge of the wafer, relative to an approximating rectangle, if relevant. As described above, the line derived from connecting the attachment site edges, of each attachment site, closest to the distal end of wafer is the attachment line.

Generally, a gap is disposed between the attachment sites of the electrical connectors. The distance between the attachment sites of the electrical connectors, i.e. the gap, is preferably between about 2 mm and about 180 mm, and more preferably between about 5 mm and about 50 mm. The electrical connectors can be edge connectors, for example, card edge connectors.

The electrical connectors can be connected to the opposite poles of a power source through electrically conductive wires. The power source can be an alternating current power source or a direct current power source. Preferably, the power source has voltage of between about 2 volts and about 40 volts and more preferably between about 4 volts and 24 volts.

The temperature gradients on the surface of the wafer are generally substantially perpendicular to the attachment line that can be defined as the x-axis. The temperature gradients are, thus, generated along a y-axis, perpendicular to the x-axis (attachment line). In other words, the temperature changes according to the distance from the attachment line. The temperature is approximately constant at equal distances from the attachment line.

Generally, the temperature is highest near the attachment line and progressively decreases with distance away from the attachment line. Preferably, the decrease in the temperature along any y-axis is approximately linear. Preferably, movement along the x direction for any value of y does not result in any substantial temperature change.

The temperature along the x direction at or near the attachment line may vary slightly. The temperatures along a line parallel to and at about 20 mm from the attachment line preferably are about the same. More preferably, the temperatures along a line parallel to and about 15 mm from the attachment line are about the same. Even more preferably, the temperatures along a line parallel to and about 10 mm from the attachment line are about the same.

The gradient apparatus preferably includes control circuitry. The control circuitry of the gradient apparatus can include, for example, a temperature sensor, a temperature controller, a relay switch and a transformer. The temperature sensor is generally physically attached to the wafer and electrically connected to the temperature controller. The relay switch and the transformer can be operatively connected between the power source and the wafer. Feedback control between the temperature sensor and the temperature controller is used to open or close the relay switch, thereby regulating power to the wafer and controlling its temperature.

The temperature sensor is generally attached to the wafer surface in the gradient apparatus. The temperature sensor is preferably positioned in the gap between the two electrical connectors of the gradient apparatus.

The temperature sensor can detect the temperature of the wafer and is associated with the upper surface of the wafer. Preferably, the temperature sensor is a resistive temperature sensor, a thermocouple, a thermodiode, a thermotransistor, thermoresistor or thermistor. More preferably, the temperature sensor is a 100 ohm platinum resistive temperature detector (RTD). Temperature controllers can be purchased from a number of commercial sources. A suitable temperature controller includes, for example, temperature controller model 982 from Watlow Engineering, Winona, Minn.

The temperature controller and the temperature sensor may be parts of separately fabricated electrical circuits. Alternatively, they may comprise a single integrated circuit.

In some embodiments, the gradient apparatus may operate without the feedback control provided by the temperature controller and sensor. The gradient can then be dependent on the power source, ambient temperature and the like.

A variety of suitable relay switches can be used in the gradient apparatus. Suitable relay switches include, for example, a solid state relay switch, a reed relay switch and the like. Preferably, the relay switch is a solid state relay switch.

A transformer can be used to change the voltage from a power source, for example, an alternating current power source, to the wafer. The transformer generally is in electrical series with the power source and the relay switch, for example, as illustrated in FIG. 1.

The apparatus may optionally be mounted in a walled structure that supports the wafer in a substantially flat manner and houses the controller. The housing may be fabricated from various suitable materials including plastic and/or metal. Preferably, the housing is plastic, such as polypropylene or polycarbonate so that the housing may be molded in an inexpensive fashion.

The apparatus may also include a support, preferably molded from electrically insulating materials such as silicone rubber, underneath the distal edge of the wafer.

The apparatus of the invention may also include a commercial personal computer, work station or a self-contained microprocessor. In one embodiment, the computer receives temperature information from the temperature sensor and executes software commands that cause the controller to open or close the relay, thereby regulating the power available to heat the wafer.

In another embodiment, the computer may be electrically attached by transmission cables to a relay controller and to an electronic sensing device (an analog to digital converter) that is electrically connected to the temperature sensor. In this embodiment, the computer receives temperature information from the analog to digital converter and executes software commands to the relay controller.

Figure 2:
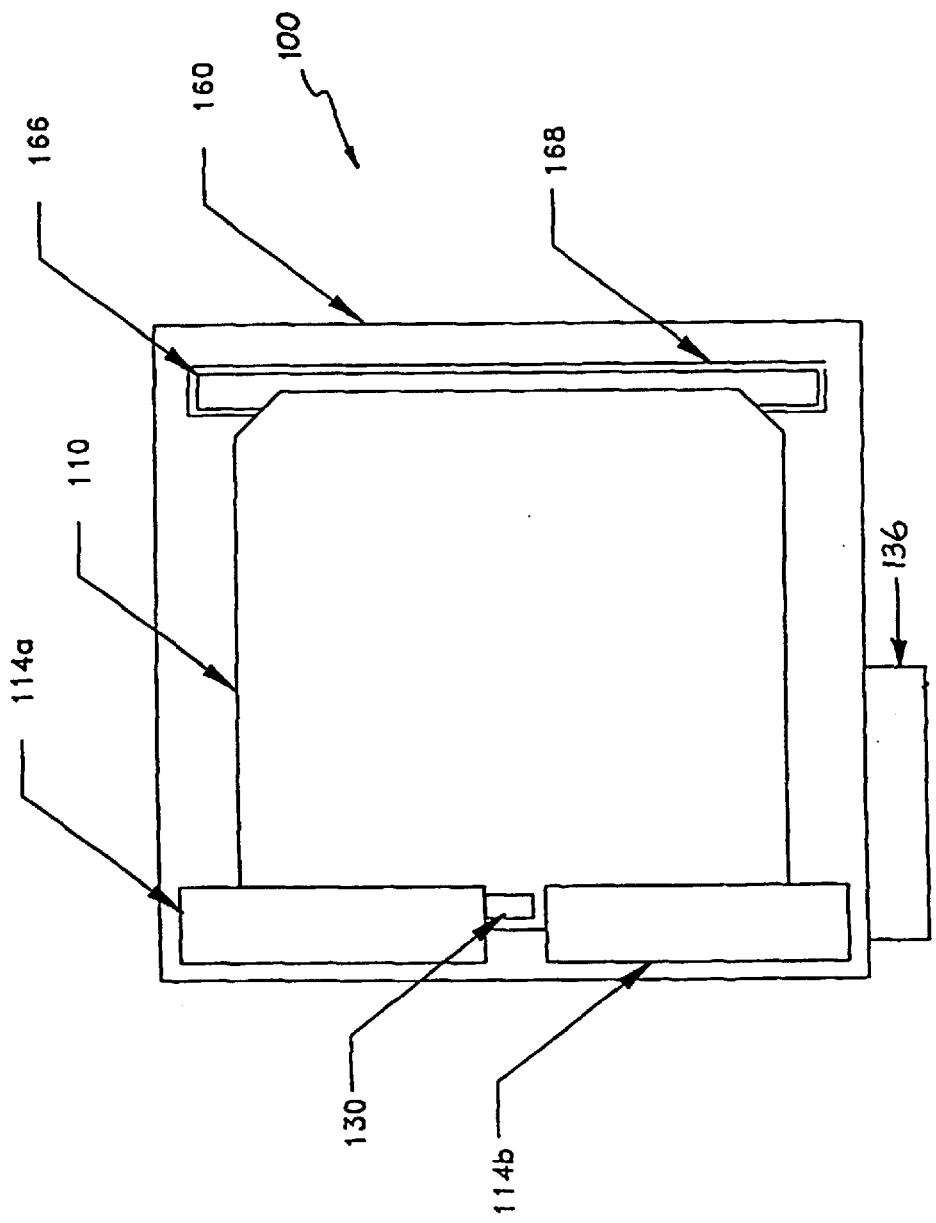
FIG. 2 is a top view of the thermal gradient apparatus.
Figure 3:
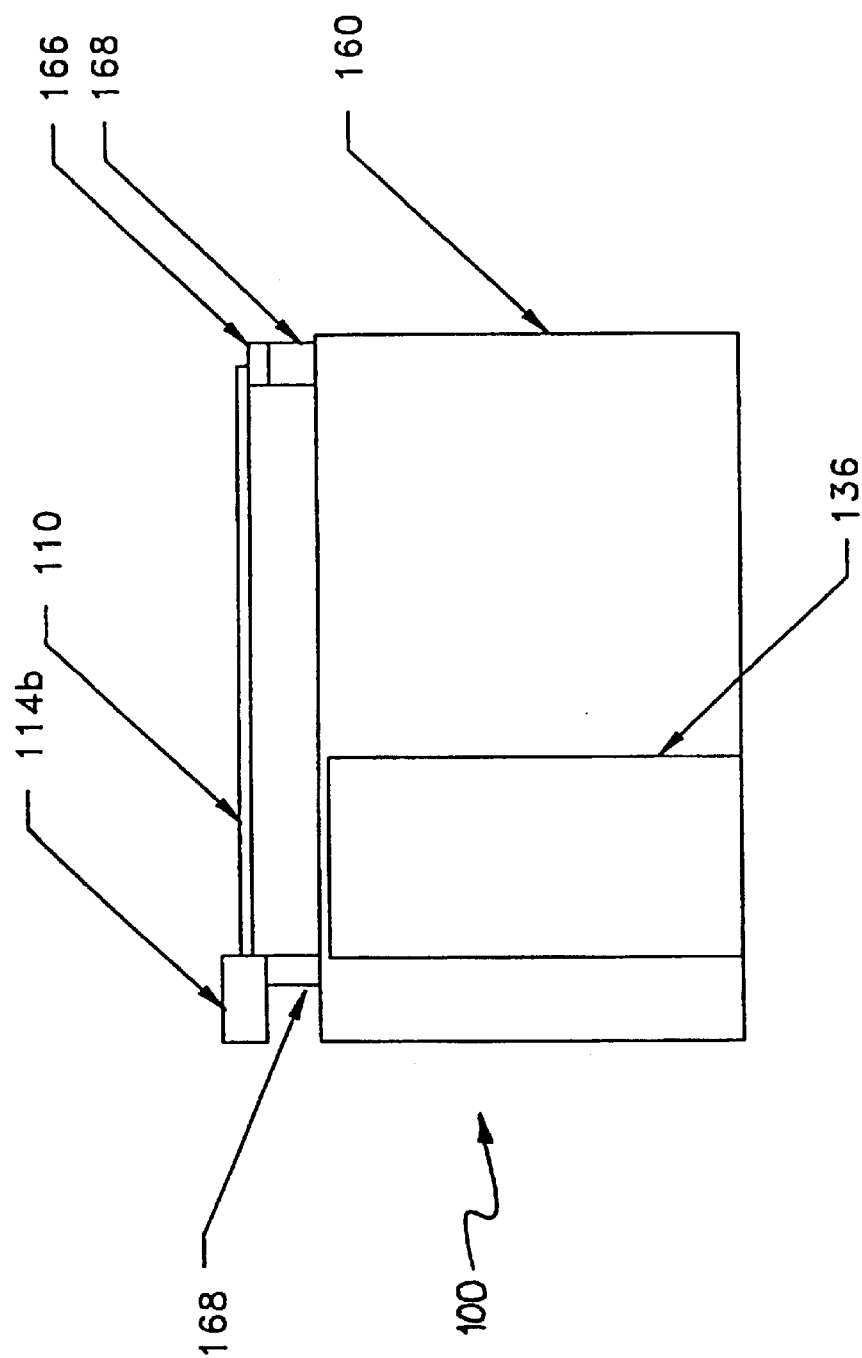
FIG. 3 is a side view of the thermal gradient apparatus of FIG. 2.

FIGS. 1–3 show an illustrated embodiment of a gradient apparatus. A schematic of gradient apparatus 100 is shown in FIG. 1. Gradient apparatus 100 includes silicon wafer 110, electrical connectors 114a and 114b and electrically conductive wires 116a and 116b. Electrically conductive wires 116a and 116b can be connected to power source 126 through control circuitry.

Control circuitry can include a number of components. In the embodiment illustrated, control circuitry includes transformer 120, temperature sensor 130, temperature controller 136 and relay switch 140. Temperature sensor 130 is positioned in gap 134 between connectors 114a and 114b. Temperature sensor 130 and transformer 120 are connected to a temperature controller 136 such as the model 982 available from Watlow Engineering, Winona, Minn. A solid state relay switch 140 is connected by electrical wire 116b in one electrical series to the controller 136.

A top view of gradient apparatus 100 is shown in FIG. 2. Gradient apparatus 100 includes silicon wafer 110 and two electrical connectors 114a and 114b attached to wafer 110 at the proximal edge. The distal edge of wafer 110 is supported by wafer gasket 166. Posts 168 support the wafer gasket 166 and the electrical connectors 114a and 114b.

FIG. 3 is a side view of apparatus 100 shown in FIG. 2. The wafer gasket 166 and housing 160 support the distal edge of wafer 110 (the end opposite the electrical connectors 114a and 114b).

B. Generation of Temperature Gradients

The gradient apparatus of the present invention can produce stable temperature gradients on a wafer when the electrical connectors of the apparatus are connected to a power source. The temperature gradient increments generated on the wafer can be small and reproducible.

The gradient apparatus can be used to establish many different gradients. In order to generate a desired temperature gradient, the temperature controller of the apparatus can be set to a desired set point temperature. The temperature on the wafer is generally highest near the attachment line and decreases away from the attachment line. The actual gradient generated on the wafer can depend on, for example, the set point temperature selected, the placement of the temperature sensor on the wafer, the electrical resistance of the card connectors, ambient temperature and also on the composition of the wafer.

The temperature detected at the attachment line is the upper limit of the temperature gradient on the wafer and is preferably within about 20° C., and more preferably, within about 10° C. of the set point temperature.

The temperature range of the gradients generated on the wafer can be manipulated by adjusting the set point temperature of the temperature controller in the apparatus of the invention. The temperature controller can be set, for example, at about 75° C. to obtain a temperature gradient of between about 75° C. and about 50° C. Similarly, the temperature controller can be set, for example, at about 45° C. to obtain a temperature gradient of between about 45° C. and 20° C.

Preferably, the apparatus generates stable temperature gradient increments of less than about 1° C. per millimeter (mm). More preferably, the apparatus generates stable temperature gradient increments of between about 0.1° C./mm and 0.5° C./mm. The ability to generate such small temperature gradient increments can be applied to many different analyses of biological/chemical molecules.

The temperature gradient on the wafer can be determined by measuring the temperature at various locations along a y-axis. A plot of temperature versus position, i.e. distance from the x-axis or attachment line, can produce a temperature gradient profile. The slope of the temperature gradient profile also can provide the temperature gradient increments generated on the wafer.

The slope of the temperature gradient profile for a given wafer and for given conditions is generally substantially reproducible. The gradient apparatus can be calibrated for a wafer and fixed by setting the current. Once calibrated, reproducible temperature gradients are generated by setting the set point of the controller.

The slope of the temperature gradient profile, thus the increments, may be decreased by additionally attaching a heating source to the wafer at the distal edge of the wafer. The presence of the connectors as described above and an additional heating source at the distal edge may result in a temperature gradient profile with a smaller slope.

The slope of the temperature gradient profile may be increased by attaching a cooling source at the distal end from the connectors. The cooling can be performed, for example, by using a fan to sweep ambient temperature across the end opposite the electrical connectors. Preferably, the cooling can be performed by thermoelectric cooling provided by a peltier device attached to the wafer, an anodized aluminum heat sink attached to the wafer at the distal end and the like.

The temperature gradient generated on the surface of the wafer can be monitored in a non-obtrusive manner with an infrared-sensitive camera system, image acquisition software, data logging software, a memory card for storing the acquired data and data plotting software. Other methods for monitoring can include methods of gradient analysis involving placement of temperature sensitive electronic circuits such as resistance temperature devices in direct contact with the wafer. The detectors, however, can act as heat sinks and distort the gradient profile.

Figure 4B:
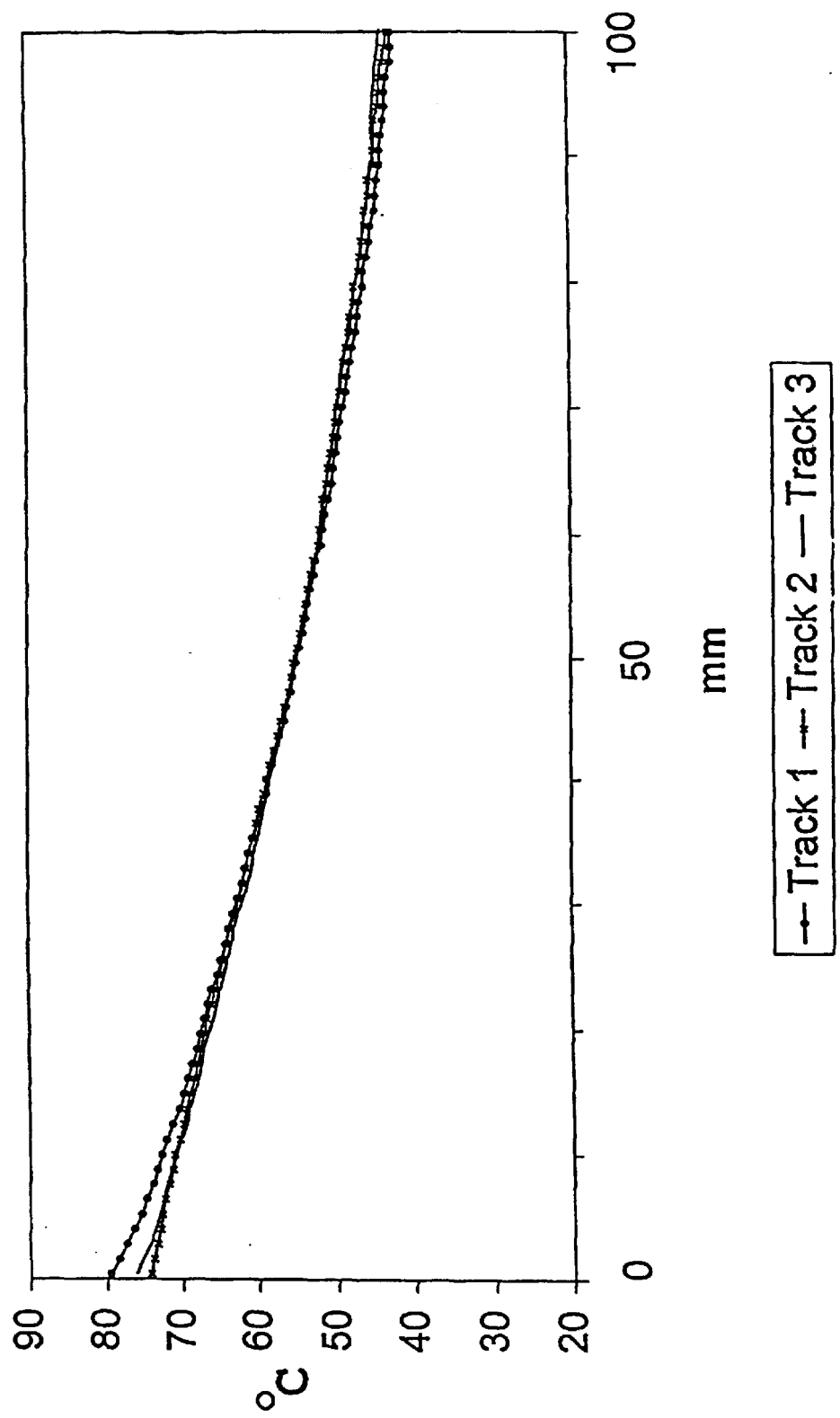

The gradient apparatus of the present invention can generate the desired temperature gradients using resistive heating and thermal conduction. In one embodiment, as shown in FIG. 4a and FIG. 4b, with an ambient temperature of about 20° C., a temperature gradient of about 0.30° C./mm was generated on the surface of a boron doped silicon wafer. In addition, the plot in FIG. 4b, indicates that the gradient generated can be monotone and substantially linear. In temperature gradient profiles described herein, the distances are measured from the attachment line, i.e. 0 mm is the attachment line.

Figure 5A:
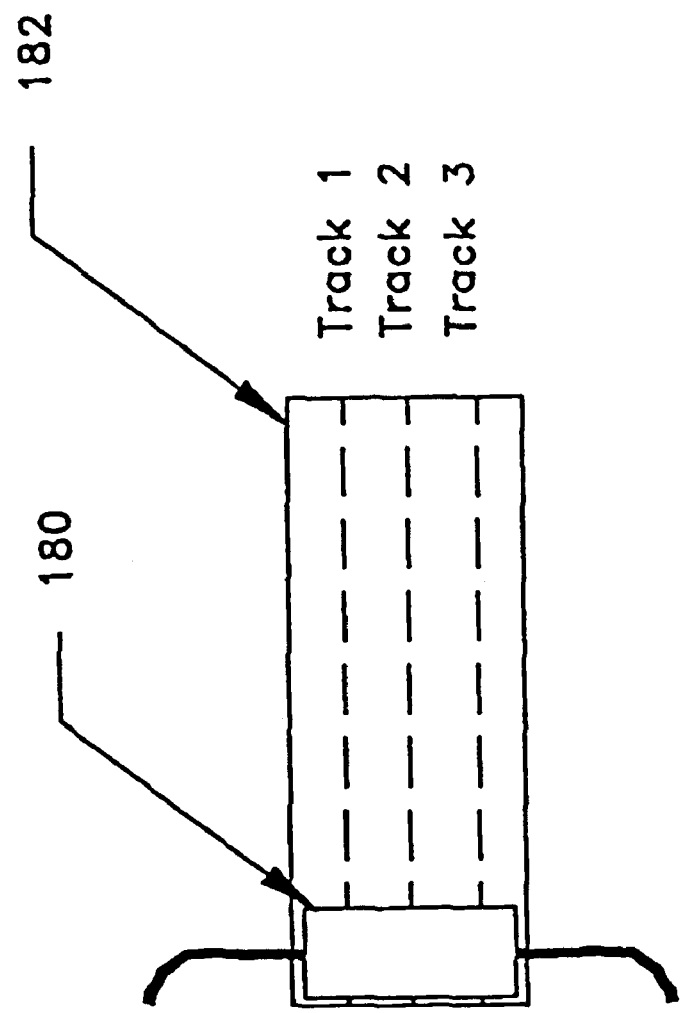
FIG. 5a is a schematic illustration of an apparatus in which a temperature gradient is formed by thermal conduction alone.
Figure 5B:
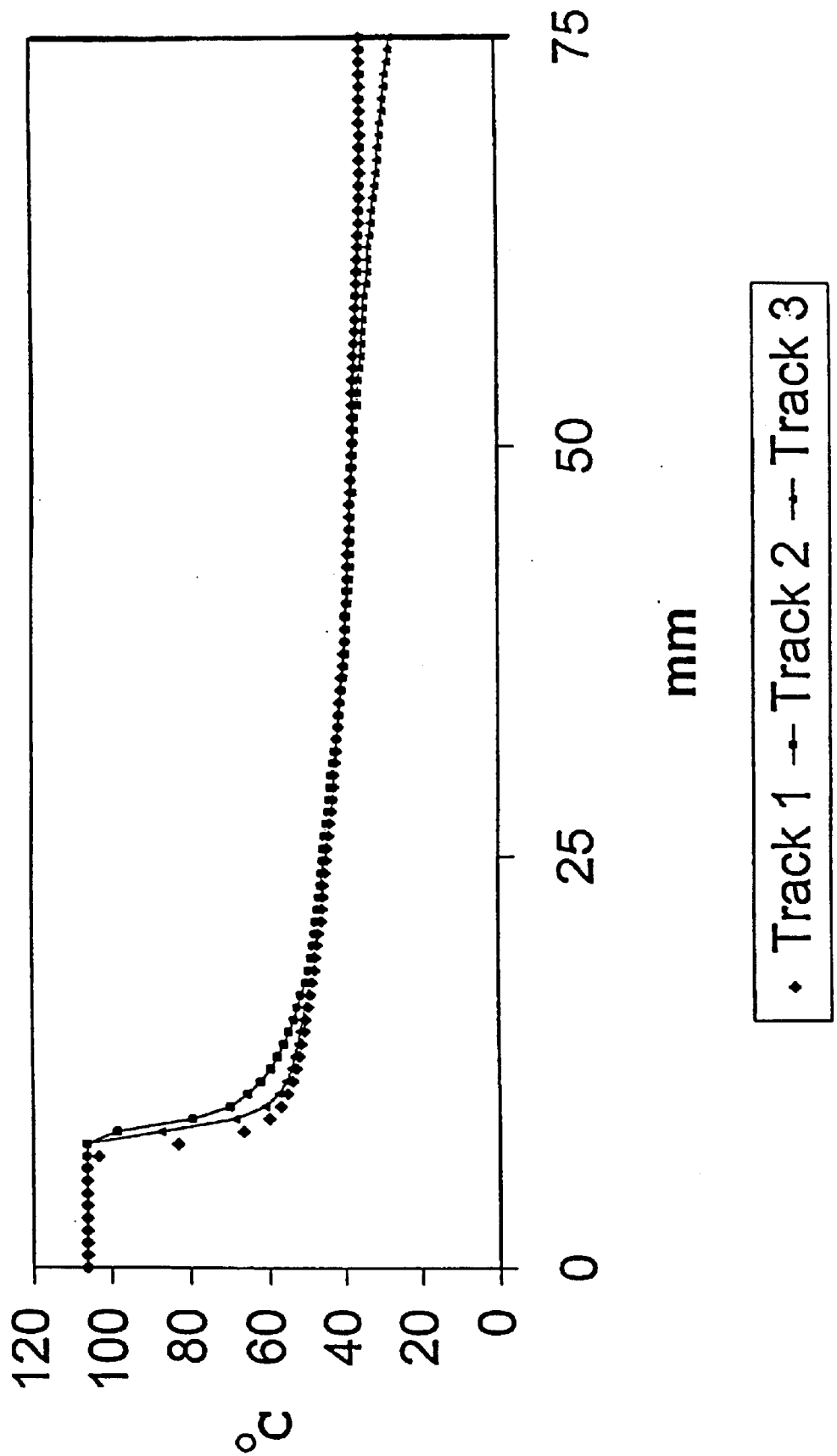
FIG. 5b is a plot of temperature versus position for three tracks indicated in FIG. 5a using a silicon wafer in the apparatus.

For comparison, an apparatus for producing a temperature gradient by thermal conduction alone (no resistive heating) is illustrated in FIG. 5a. The thermal conduction apparatus of FIG. 5a includes surface 182 that can be either a silicon wafer or a glass microscope slide heated at one end with a 20 ohm resistor. As shown in FIG. 5b, the temperature gradient when the surface is of a silicon wafer is about 10° C./mm. The method of the invention described herein, thus, can produce a temperature gradient that is approximately 30 times shallower than the gradient produced by thermal conduction alone on a wafer.

As shown in FIG. 5c, the gradient produced when the surface is of a microscope slide can be approximately 3.7° C./mm using thermal conduction alone. The methods described herein, thus, can produce a temperature gradient that is approximately 10 times shallower than the gradient produced by conduction alone on a glass microscope slide.

C. Application of Temperature Gradients

The temperature gradients generated on the semiconductive wafer using the gradient apparatus described herein can be transferred to one or more strata placed on the wafer. The thermal gradients on the strata can, in turn, be used to assess the thermal stabilities of molecules including, for example, nucleic acids, polypeptides, carbohydrates, lipids, drugs, ligands, combinations thereof and the like. The thermal stability of complexes of the chemical/biological molecules and their respective binding partner(s) can be determined using the methods described herein.

The molecules to be analyzed are generally placed on a stratum such as a glass microscope slide, a silicon chip, an acrylamide gel, nitrocellulose, a charged nylon membrane and the like. By placing the stratum containing the molecules on the wafer of the invention, performing biological manipulations, and then removing the stratum from the wafer, the wafer can be reused many times. When biological manipulations are carried out, as shown in the examples below, the temperature gradient on the wafer is transferred to the stratum.

Samples that can be analyzed in the gradient apparatus can include any number of chemical/biological molecules. Samples can include isolated or purified macromolecule preparations such as isolated nucleic acids and polypeptides. Samples can also include drugs, hormones, and the like. In addition, samples can include tissues, parts of tissues, partially purified tissue extractions, cell preparations, living cells and other biological material.

Suitable strata can include, for example, glass chips, microscopic glass slides, acrylamide gels, fluidic cells, liquids, coverslips for the glass slides and the like. Strata can be any other strata that are employed in medical diagnostics, molecular biology and cellular biology at temperatures, preferably ranging from ambient temperature to about 100° C. The thermal conductivity of the strata can vary. Surprisingly, the temperature gradient can be transmitted to strata that have low thermal conductivity. The temperature gradient can be transferred to glass, for example, that has a thermal conductivity between about 0.1–1.0 watts/meter/° K.

Stratum can include one component such as a DNA chip or a protein chip. The stratum can also include a plurality of components, for example, a fluidic cell having a base, a glass slide, liquid and a cover, a slide assembly having two slides with acrylamide gel disposed between the slide, and the like.

In particular, a temperature gradient on a wafer of the invention can be transferred to the surface of a glass or silicon DNA chip in the gradient apparatus. Thus, any samples that may be present on the DNA chip would be subjected to the corresponding temperature of the DNA chip at the particular location.

Figure 6A:
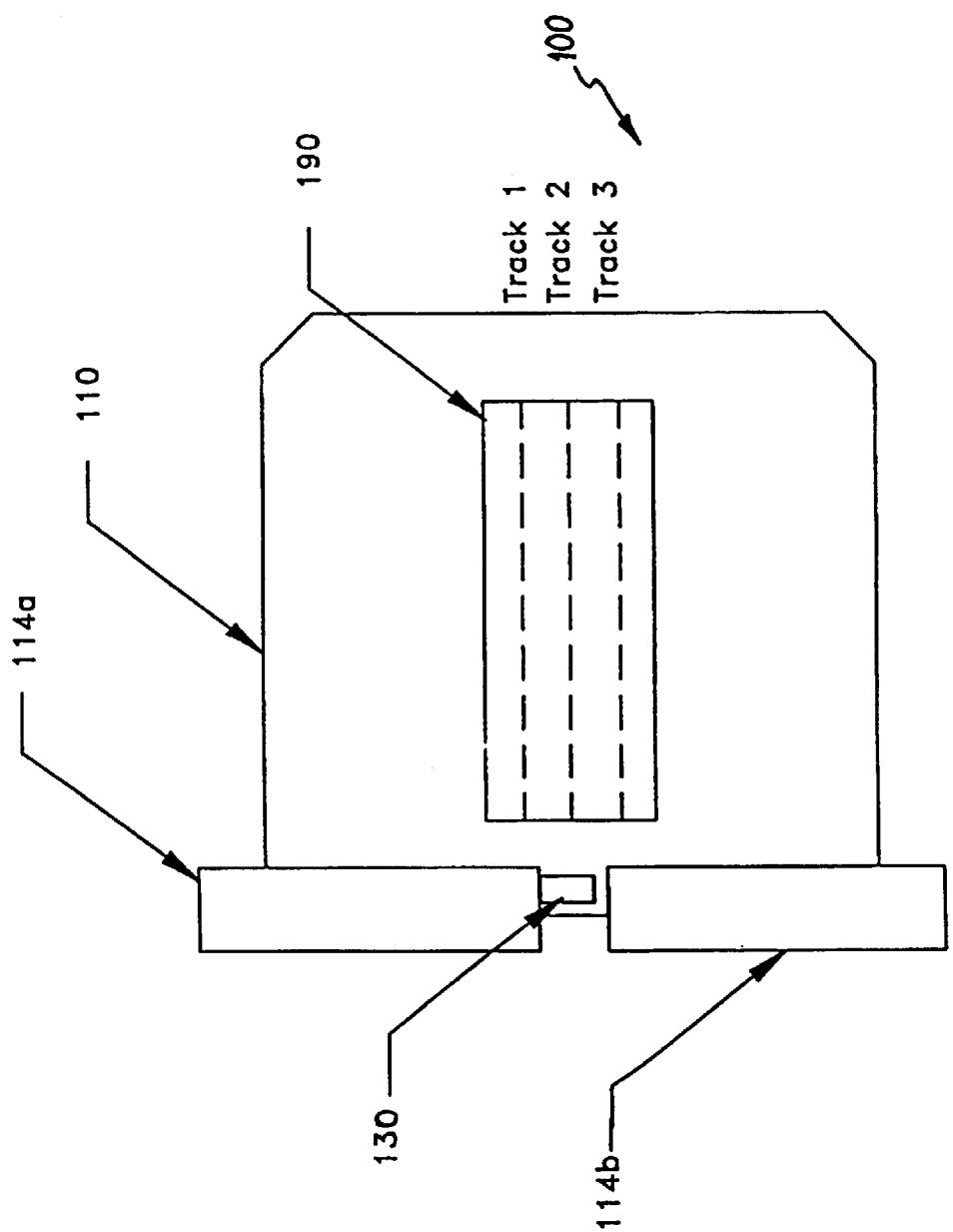
FIG. 6a is a top view of a thermal gradient apparatus with a glass slide on the wafer.

In one illustrated embodiment, glass microscopic slide stratum 190 is placed on wafer 110 of the invention as shown in FIG. 6a. The temperature gradients along the y-axes of the slide were collected and analyzed by an infrared imaging system and then plotted in FIG. 6b. These results demonstrate that y-axes on microscopic glass slide 190 have temperature gradients of approximately 0.3° C./mm.

The temperature gradients along y-axes of the slide when the controller's set point was adjusted to 40° C., 45° C., 50° C., 55° C., 60° C., 65° C., 70° C., 75° C. and 80° C., respectively are plotted in FIG. 6c-FIG. 6k. These results demonstrate that the invention can produce gradients with slopes between 0.1° C./mm and about 0.5° C./mm. The slope of the gradient is determined by the setpoint. Thus, setpoints of 40° C., 70° C. and 80° C. generate, respectively, gradients with slopes of 0.1° C./mm, 0.3° C./mm, and 0.5° C./mm.

Figure 7A:
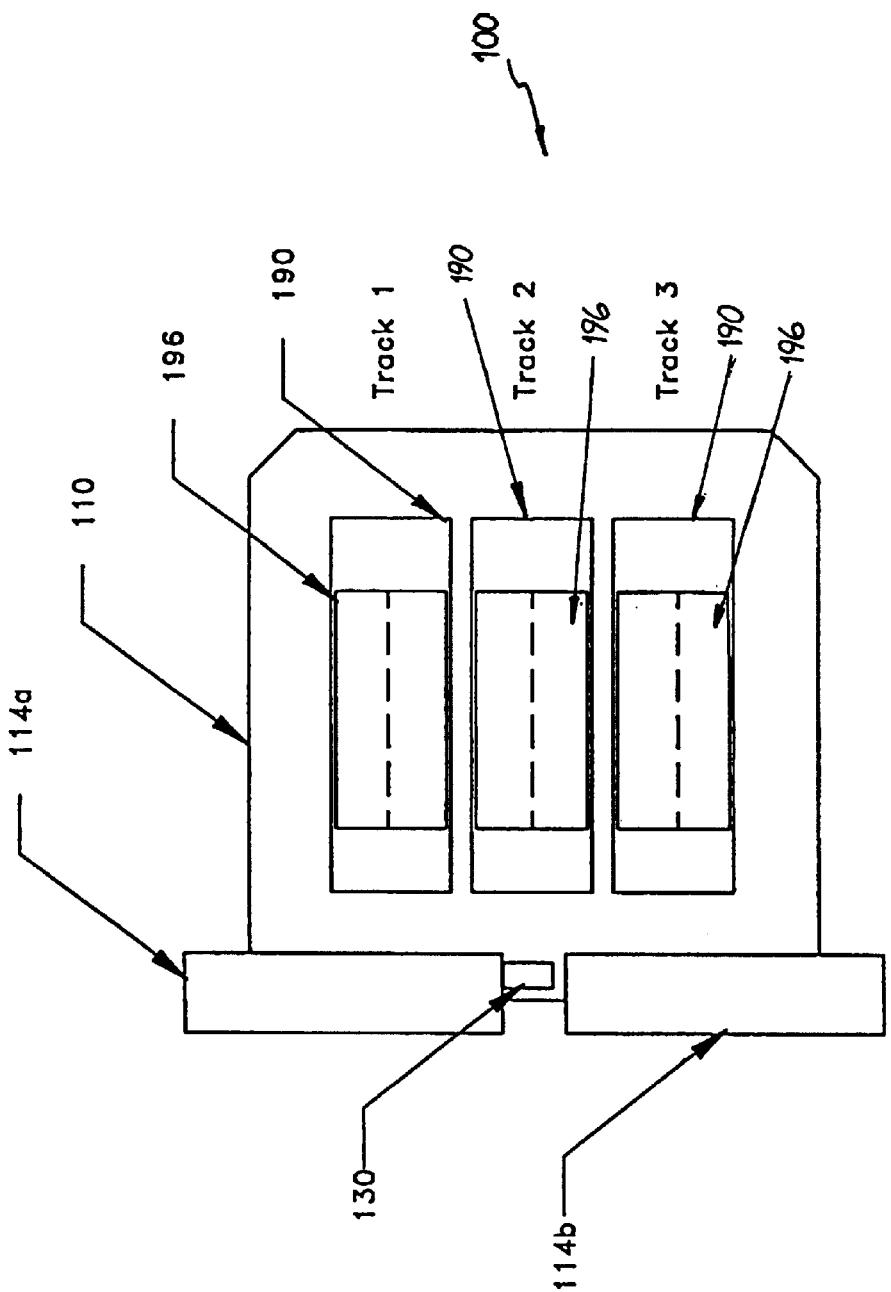
FIG. 7a is a top view of a thermal gradient apparatus with three glass slides on the wafer. Each slide has a drop of water that is covered by a coverslip.

In another illustrated embodiment shown in FIG. 7a, apparatus 100 includes three glass microscope slides 190 placed on silicon wafer 110. A small drop of water, approximately 50 microliters in volume, can be placed onto the center of each of the three microscopic slides. Each drop of water can then be covered with a glass microscope slide coverslip 196. The three slide assemblies can then be placed on wafer 110 with a preformed temperature gradient and analyzed by thermal imaging after one minute. The plotted results of the apparatus in FIG. 7a are shown in FIG. 7b. The results in FIG. 7b indicate that the y-axes on coverslips 196 atop each of the slides 190 can have temperature gradients of approximately 0.30° C./mm.

Figure 8A:
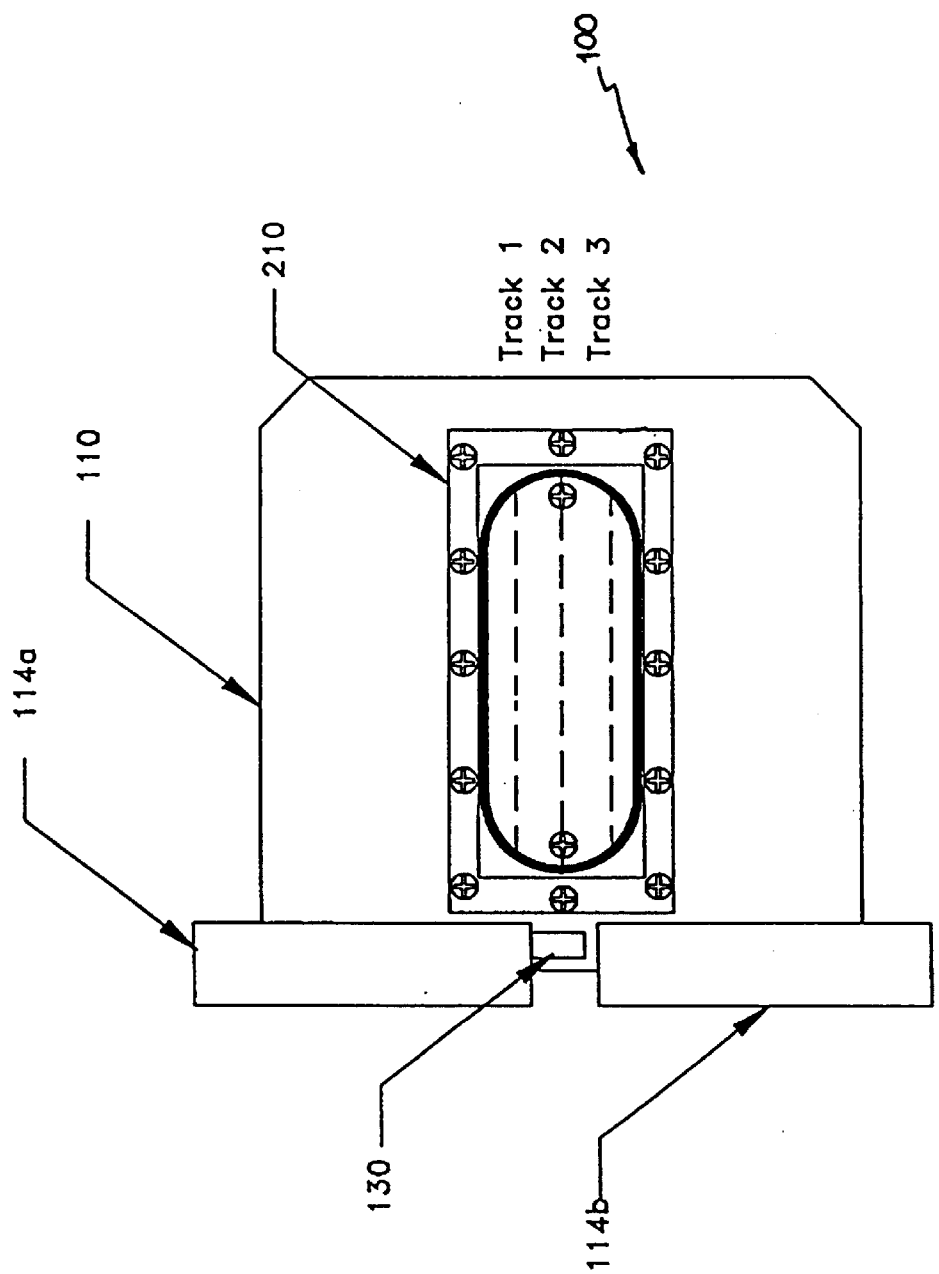
FIG. 8a is a top view of a thermal gradient apparatus with a fluidic cell on the wafer.
Figure 8B:
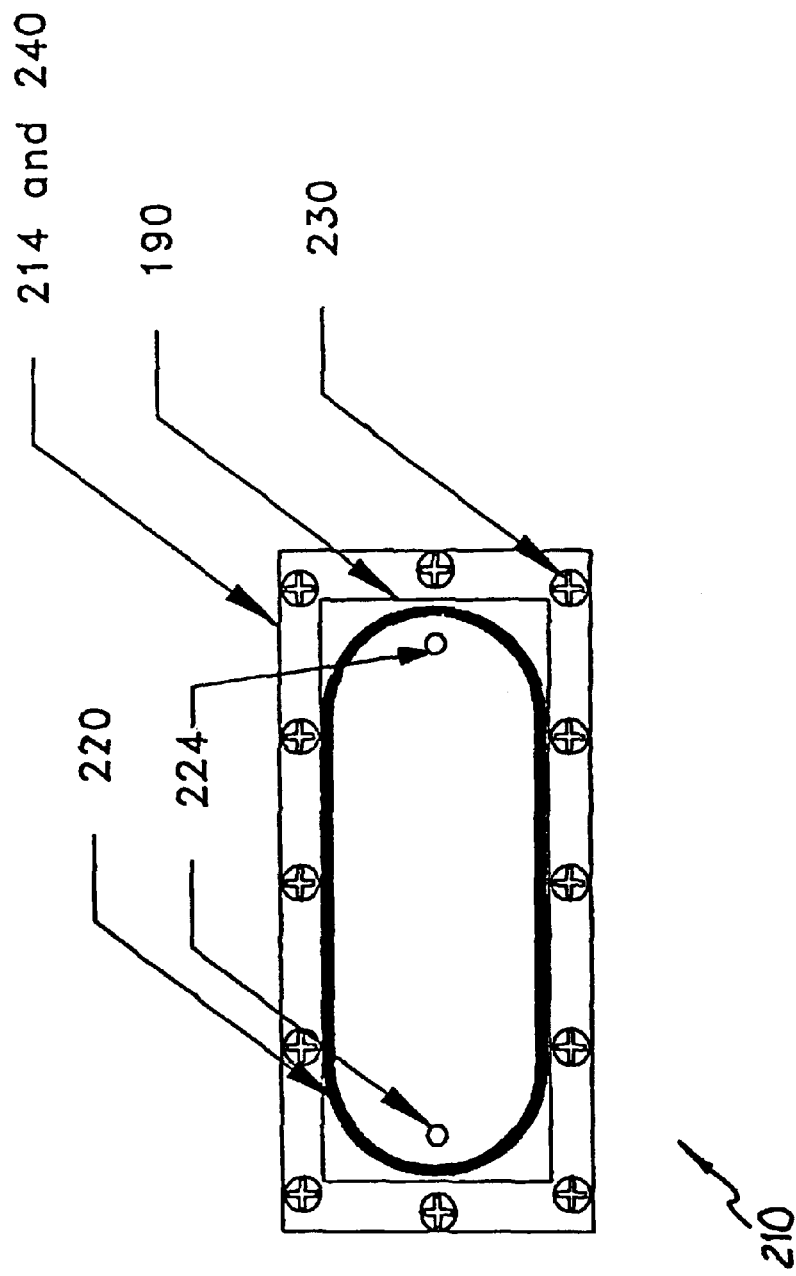

In another illustrated embodiment shown in FIG. 8a, apparatus 100 with a DNA chip fluidic cell 210 containing glass microscopic slide 190 and liquid film with a volume of approximately 120 microliters is shown disposed on wafer 110. FIG. 8b illustrates a more detailed top view of the fluidic cell 210 shown in FIG. 8a. Assembled fluidic cell 210 can include base 214, preferably made from lucite, with a machined recess 218 that can accommodate microscopic slide 190, a machined groove fitted with an o-ring 220, lucite lid 240 with two filling holes 224 and machine screws 230 that tighten the lid against o-ring 220. In use, a glass microscopic slide with DNA is placed in the cell, the lid is placed on the gasket and the machine screws are used to tighten the lid against the gasket. The tightened cell can be water-tight, and has an airspace, approximately 0.1 mm high between the surface of the slide and the lid, with a volume of approximately 120 microliters. Fluid can be introduced through one of the fill holes and both fills can then be sealed. The assembled cell with a fluid film atop the slide is placed on the wafer of the invention with a preformed temperature gradient and the temperature along the lucite lid of the cell is collected and analyzed by an infrared imaging system and then plotted. A plot of the temperature gradients on the lid of cell is shown in FIG. 8d and indicates that the y-axes of the lid of the cell can have temperature gradients of approximately 0.3° C./mm.

Figure 9B:
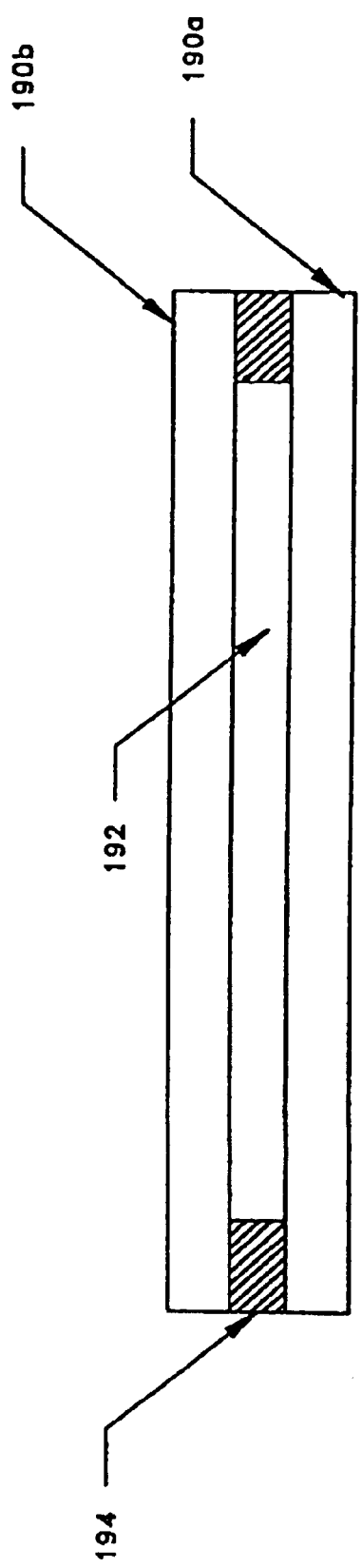
Figure 9C:
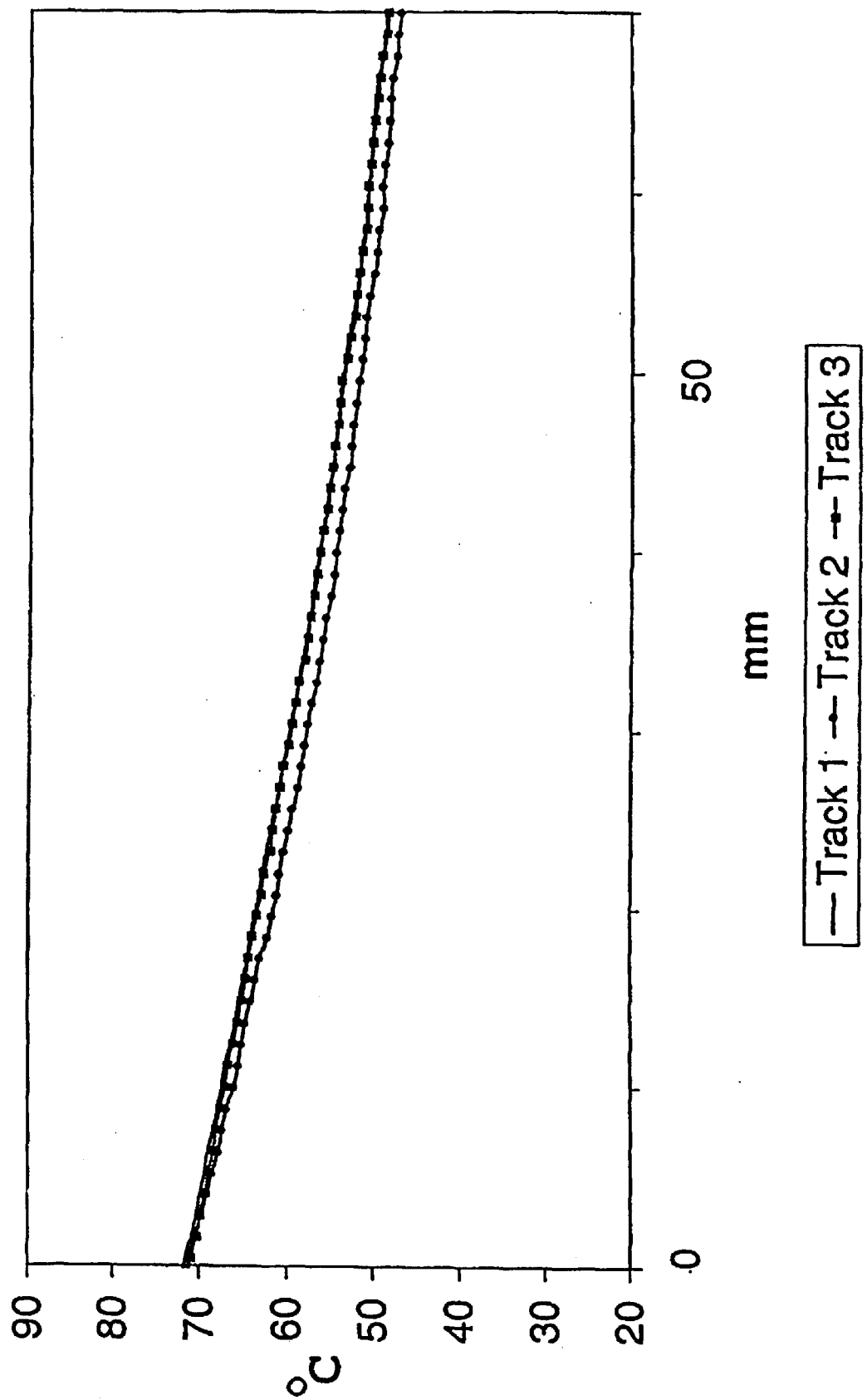

The temperature gradients can also be transmitted to and through an acrylamide gel disposed between two glass slides. Two glass slides with acrylamide gel between them can be placed on the wafer. In FIG. 9a and FIG. 9b, two glass slides 190a and 190b are disposed on the wafer with an acrylamide gel between glass slides 190a and 190b. The linear tracks, shown in FIG. 9a, are the tracks on the upper surface of top glass slide 190b. The temperature on the upper surface of the top glass slide 190b can be measured using an infrared camera as described above. The upper surface of the top glass slide 190b can have a temperature gradient as shown in FIG. 9c. The presence of temperature gradients on the top glass slide 190b can indicate that the strata underneath the glass slide 190b have approximately similar temperature gradients. Thus, the bottom glass slide 190a and the acrylamide gel between the glass slides 190a and 190b can have approximately similar temperature gradients as the top glass slide 190b. The samples in the acrylamide gel can, thus, be exposed to the temperature gradients.

Samples can be placed on the stratum in order to assess thermal stability at a variety of temperatures. Generally, a plurality of samples are placed on the stratum at different locations on the stratum. As described above, samples that are placed at differing positions along a y-axis perpendicular to the attachment line, i.e. samples having different y-coordinates, are generally exposed to different temperatures. Samples that are placed at the same y-coordinates but at differing points along an x-axis, i.e. samples have differing x-coordinates but same y-coordinates, are generally exposed to about the same temperature.

The samples may be placed on the stratum using a variety of techniques known in the art. A number of nucleic acid samples, for example, may be immobilized on DNA chips as described in U.S. Pat. No. 5,925,525 to Fodor et al., U.S. Pat. No. 5,919,523 to Sundberg et al., U.S. Pat. No. 5,837,832 to Chee et al. and U.S. Pat. No. 5,744,305 to Fodor et al. which are incorporated herein by reference. Nucleic acid molecules, for example, can also be directly synthesized on the DNA chip by solid phase synthesis on derivatized chips. The samples may also be immobilized onto the stratum by chemical crosslinking using crosslinking agents, ultraviolet crosslinking and the like. Crosslinking agents and methods of crosslinking are known in the art.

The sample placed on the stratum can include a single type of molecule such as a preparation of a single stranded nucleic acid molecule, a preparation of an antigen and the like. Potential binding partners of these molecules, for example, the complementary strand of the single stranded nucleic acid, the antibody of a antigen:antibody complex can be subsequently added to the stratum and allowed to bind to the immobilized sample on the stratum. A labeled probe can be added to the stratum that directly or indirectly binds to the molecules immobilized on the stratum. In some embodiments, the labeled probe is the binding partner of the immobilized molecule.

The labeled probe can provide a means for detecting the thermal stability of the molecules at the specific location on the stratum. Detection of the thermal stability can be performed by observing, locating and/or quantifying the label that is specifically associated with the sample on the stratum. The signal generated for detection of thermal stability can be derived directly or indirectly from the interaction between the sample and the labeled probe. Detection and/or measurement of the signal of the labeled probe can then be indicative of and/or correlated with the thermal stability of the molecules on the stratum.

The label of the labeled probe can be for example, a radioactive atom, a fluorophore, a chromophore, a chemiluminescent reagent, an enzyme capable of generating a colored, fluorescent or chemiluminescent product, or a binding moiety capable of reaction with another molecule or particle which directly carries or catalytically generates the signal. Binding moieties can be attached to the probe and include, for example, biotin that binds tightly to streptavidin or avidin and digoxygenin that is tightly bound by anti-digoxygenin antibodies. The avidin, streptavidin and antibodies, in turn, are easily attached to chromophores, fluorophores, radioactive atoms, and enzymes capable of generating colored, fluorescent or chemiluminescent signals.

Detection of the labeled probe, bound directly or indirectly to the molecules of the sample, can include detecting fluorescence, chemiluminescence, radiolabels and the like by one or more of microscopy, photography, autoradiography and fluorimetry. Detection can also be measured, for example, by measuring the visible or ultraviolet absorbance.

In some embodiments, the sample can include a binding complex, i.e. two members of a binding complex, such as a double stranded nucleic acid molecule, a receptor:ligand complex and the like. The binding complex can be immobilized onto the stratum. When exposed to a temperature gradient, the binding complex, if dissociated, may exhibit a measurable property. For example, a binding complex may have a measurable fluorescence that changes upon dissociation.

The chips generally include a plurality of samples. All of the samples on the chip may be the same. Alternatively, each track of the chip may contain different samples. Within each track, the samples are preferably equivalent so that the equivalent samples can be exposed to different temperature. Track, as referred to herein, is a row of samples along one of the y-axis, i.e. the samples in a track have the same x-coordinate and different y-coordinates.

In the apparatus of the invention, a pair of electrical connectors are attached to the wafer as described above, and connected to a power source. In preferred embodiments, the temperature controller of the gradient apparatus is set to a desired temperature determined by the nature of the samples to be analyzed.

The samples on the chip are exposed to different temperatures that can be directly related to position on the stratum due to the gradient profile of the wafer which is efficiently transferred to the stratum. Generally, the slope of the temperature gradient on the stratum is approximately similar to the slope of the temperature gradient on the wafer.

The interaction between the labeled probe and the sample or samples at various temperatures can be determined since the samples at different positions on the stratum are exposed to different temperatures. Analysis of the information generated by these type of studies can identify the thermal dissociation temperature of the specific complexes formed; that is, the temperature at which the members of the binding complex no longer remain stably associated with each other because of thermal instability associated with, for instance, temperature-dependent changes in molecular shape, or temperature-dependent rupture of hydrogen bonds.

In some embodiments, for example, a detectable signal, generated by the labeled probe and indicative of a nucleic acid hybridization event, may be present for samples, at locations specifying temperatures of 60° C. and 60.3° C., but not at 60.6° C. The hybridization between the samples and the labeled probe, thus, is stable at temperatures up to about 60.3° C., but is not stable at temperatures above about 60.6° C.

The apparatus of the invention can be used to determine the thermal stability of nucleic acid duplexes by conducting nucleic acid hybridizations on a stratum on the wafer. Methods for nucleic acid hybridization and thermal dissociation are known in the art. As applied to DNA chips with the present invention, they would involve the following sequential steps: obtaining or creating a DNA chip containing the desired array of single stranded nucleic acid molecules immobilized on its surface; obtaining or creating a suitable labeled nucleic acid probe; annealing the labeled probe to the immobilized nucleic acids of the DNA chip disposed on the wafer having a temperature gradient; removing the unhybridized probe by repeating washing; and detecting the remaining hybridized probe. The labeled probe can be, for example, a fluorescently labeled, short single stranded DNA molecule between about 12 nucleotides long and about 20 nucleotides long. The results of such analyses would provide a graphic representation of the temperature-dependence of nucleic acid hybridization.

The present invention can include methods of determining the stabilities of nucleic acid primers used in polymerase chain reaction (PCR). PCR is a method of amplifying nucleic acid target sequences. PCR is commonly used, and is described, for example, in PCR, A Practical Approach; M. J. McPherson, P. Quirke, and G. R. Taylor, eds. IRL Press, Oxford, UK, 1991.

PCR is a technique involving multiple temperature cycles that result in the geometric amplification of specific polynucleotides present in a test sample, i.e. target sequences, each time a cycle is completed. One of the steps in this amplification of target sequences is the hybridization of a single stranded oligonucleotide referred to as a primer to a region close to or within the target sequence. Primers preferably are deoxyribonucleotides. The primers can be between about 12 and about 50 nucleotides in length and contain base sequences with Watson-Crick complementarity to sequences on one strand of the target sequence.

The primers anneal to the target sequence in order for the amplification to occur. The temperature at which the primer is allowed to anneal with the target sequence is referred to as the annealing temperature. A desirable annealing temperature is generally high enough to suppress annealing at non-specific sites but low enough to allow for duplex formation between the complementary primer:target sequences. At annealing temperatures that are too low, the primer may anneal at non-specific sites. Thus, it is desirable to identify the highest temperature at which primer:target sequence duplexes can be maintained in solution.

In one embodiment of the present invention, the dissociation temperature of specific PCR target:primer duplexes can be determined. Target DNAs can be placed, for example, in rows along the y-axis of the stratum. The stratum can then be placed in a fluidic cell, exposed to a temperature gradient, incubated with labeled primers, and washed. The resulting pattern of labeling can identify the thermal stability of the primer:target duplex. FIG. 10a and FIG. 10b illustrate an example of this embodiment and a hypothetical result. A DNA chip 270 with target DNA arrayed in a row along the y-axis is shown in FIG. 10a. The target DNA on the chip is exposed to a gradient of between about 40° C. and about 70° C., and hybridized with a fluorescent primer. After washing to remove unbound primer, the distribution of label along the y-axis is determined. One hypothetical result is illustrated in FIG. 10b. The result in FIG. 10b shows that a labeled probe is present at a position in the stratum corresponding to about 55° C., but is not present at a position corresponding to about 55.6° C. The optimum temperature for this primer:target combination, thus, is about 55.0° C.

Figure 11B:
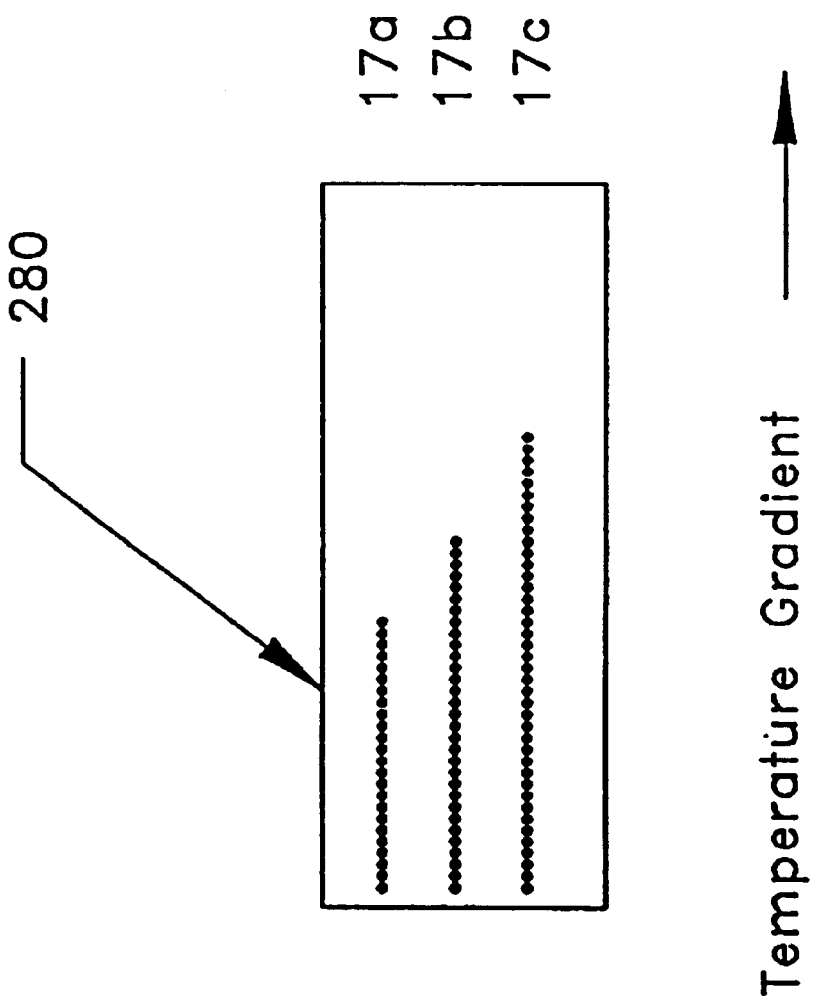

In another embodiment, the temperature gradient on a wafer can be used to identify one or more mismatches between related nucleic acid molecules. In particular, the thermal stability information obtained from performing nucleic acid hybridizations in the gradient apparatus can be used to identify the percentage of mismatch between two nucleic acid molecules. FIG. 11a illustrates one method of using the gradient apparatus for determining thermal stabilities of closely related nucleic acid molecules. Three samples of DNA differing by one base can be immobilized on a chip and analyzed. Each of the samples can be placed on a different track with aliquots of the same sample placed at different positions within the track. A labeled oligonucleotide probe that is exactly complementary to one of the three DNA samples and covering the area of the base mismatch(es) in the other two DNA samples can be added to DNA samples on the chip. The data derived from such a study can result in data, for example, as shown in FIG. 11b. Using this method a single mismatch between the labeled probe and the DNA sample can be detected.

In FIG. 11a and FIG. 11b, DNA chip 280 has three different DNA molecules 17a, 17b, and 17c arrayed in parallel rows. Molecule 17b differs from molecule 17c by one base change, and molecule 17a differs from molecule 17c by two base changes. This DNA chip can be placed in a fluidic cell, hybridized to a labeled probe exactly complementary to molecule 17c and washed to remove unbound labeled probe. One possible result is the distribution of labeled probe along the y-axis for each sample as shown in FIG. 11b. The highest stability is seen between DNA molecule 17c and the probe, followed by DNA molecule 17b. The probe and DNA molecule 17a form the least stable complex. This result is consistent with the fact that there are no mismatches between DNA molecule 17c and the probe and that there is one mismatch between DNA molecule 17b and the probe. This result is also consistent with the fact that there are two mismatches between DNA molecule 17a and the probe. The present invention, thus, can be used to identify single base differences between DNA molecules.

The thermal stabilities of various binding complexes can also be evaluated using the gradient apparatus of the present invention. The binding complexes may include, but are not limited to, polypeptide:nucleic acid complexes, nucleic acid complexes, polypeptide:polypeptide complexes such as antigen:antibody complexes, polypeptide:carbohydrate complexes, polypeptide:lipid complexes, polypeptide:hormone complexes, receptor:drug complexes and the like. In particular, the thermal stability of antigen:antibody, enzyme:substrate, and receptor:ligand complexes can be established.

One member of the binding complex can be immobilized on the stratum. The second member of the binding complex is preferably added to the stratum and allowed to bind to the immobilized member to form a binding complex. One of the members of the binding complex may include a label, preferably the second member. Alternatively, a labeled probe may be added that interacts with only the binding complex and is indicative of the presence of a complex.

In some embodiments, binding complexes may be immobilized. The detection methods can include signals indicative of either the presence of the binding complex or dissociation of the binding complex.

In one embodiment, monoclonal antibodies directed against different epitopes of a single antigen can be immobilized in rows along y-axes on a protein chip. Using a temperature gradient, for example, between about 20° C. and about 45° C. and a labeled antigen probe, binding stabilities can be determined using procedures similar to the procedures described for DNA chips above. Briefly, the labeled antigen probe can be added and allowed sufficient time to bind to the monoclonal antibodies on the chip. Unbound labeled antigen can be washed away. The sites with bound labeled antigen can be identified using any of the protocols described above and correlated with the temperature at the site. The results can provide thermal stability information related to the various antigen:antibody complexes on the chip.

The strength of interaction between a polypeptide receptor and specific hormones, drugs, and/or other ligands also can be analyzed. Natural hormones, for example, and their synthetic analogs can be chemically linked in rows parallel to the y-axis of a stratum. Using a temperature gradient, for example, between about 20° C. and about 45° C., the labeled receptor probe, and the procedures described above, the thermal stabilities of receptor:hormone complexes can be determined.

Candidate drugs for therapeutic use can be chemically linked in rows parallel to the y-axis of a stratum. Using a temperature gradient, for example, between about 20° C. and about 45° C., labeled drug receptor probe, and the procedures described above, the thermal stabilities of individual receptor:drug complexes can be assessed.

The discussion described herein relates to some applications of the temperature gradients generated on a semiconductive wafer. The use of thermal gradients is not limited to only the applications described herein. Other applications of using the thermal gradients are also contemplated by the inventors and will be apparent to those skilled in the art.

EXAMPLES

Example 1

Generation of a Temperature Gradient on a Wafer

This example illustrates the generation of a temperature gradient on a silicon wafer by resistive heating and thermal conductivity. This example also compares the gradients of the invention with a temperature gradient formed by thermal conductivity alone.

Temperature gradient formed by resistive heating and thermal conductivity gradient was formed with an apparatus shown in FIGS. 1–3. A 114 mm×114 mm×0.6 mm boron doped silicon wafer was diced from a circular 150 mm wafer purchased from WaferNet (San Jose, Calif.). Card edge connectors were connected to the wafer and to the power source. —The temperature controller (model 982; Watlow Engineering; Winona, Minn.), was set to about 75° C. The temperature controller determined temperature with the electrical signal received from a temperature sensor that was a 100 ohm platinum RTD (Minco; Fridley, Minn.). The temperature controller/temperature sensor maintained the temperature at about 75° C. by the technique of proportional integration differentiation (PID) looping known in the art. The temperature determined by the controller was within 1.0° C. of the set point within five minutes of operation, and stayed at 75° C.±0.5° C. indefinitely. After the set point had been attained, the temperature profile of the wafer's surface was taken with an IR SNAPSHOT digital camera (Infrared Solutions: Plymouth, Minn.).

FIG. 4a shows three parallel tracks on the surface of the wafer, perpendicular to the attachment line drawn between the connectors of the invention, each separated by approximately 5 mm. The temperature versus position plot along these tracks, shown in FIG. 4b, has three lines that were approximately linear, with slopes of approximately 0.3° C./mm.

A thermal conductivity gradient was formed with an apparatus comparable to the apparatus depicted in FIG. 5a.

A 20 ohm resistor was glued to one end of a 25.4 mm×76.2 mm×0.6 mm silicon wafer. The resistor received 10 volts of alternating current from a variable-power transformer, and thereby provided heat to one end of the wafer. One hour after power was provided to the resistor, the temperature profile of the surface of the wafer was determined as described above.

FIG. 5a showed three parallel tracks on the surface of the wafer, perpendicular to the resistor, each separated by about 5 mm. The temperature versus position plot along these tracks, shown in FIG. 5b, has three approximately exponential curves, each with a slope of approximately 10° C./mm.

Comparison of the plots in FIG. 4b and FIG. 5b demonstrated that the gradient apparatus of the invention (resistive heating with thermal conduction) produced a shallow linear gradient extending at least 100 mm from the source of power, while thermal conductivity alone produced a steep exponential gradient that essentially ends within 10 mm of the source of power.

Example 2

Generation of a Gradient on a Glass Slide

This example compares the gradient formed on the surface of a glass slide by resistive heating and thermal conductivity to the gradient formed by conductivity alone.

The temperature gradient formed by resistive heating and thermal conductivity was generated as described in example 1. A glass slide having dimensions of about 25 mm×75 mm×1 mm was placed on the wafer as indicated in FIG. 6a. The temperature gradient was visualized as described in example 1.

FIG. 6a shows three parallel tracks on the surface of the glass slide, each separated by about 5 mm. The temperature versus position plot along these tracks, shown in FIG. 6b, has three lines that were approximately linear, with slopes of approximately 0.3° C./mm.

A gradient with thermal conductivity alone was formed with the apparatus described in example 1 and shown in FIG. 5a. A 20 ohm resistor was glued to one end of a 25.4 mm×76.2 mm×1.0 mm glass slide. The resistor received 10 Volts of alternating current from a variable-power transformer, and thereby provided heat to one end of the slide. One hour after power was provided to the resistor, the temperature profile of the surface of the wafer was determined as described in example 1.

FIG. 5a shows three parallel tracks on the surface of the glass slide, each separated by about 5 mm. The temperature versus position plot along these tracks, shown in FIG. 5c, produced three exponential curves, each with slopes of approximately 3.7° C./mm.

Figure 6B:
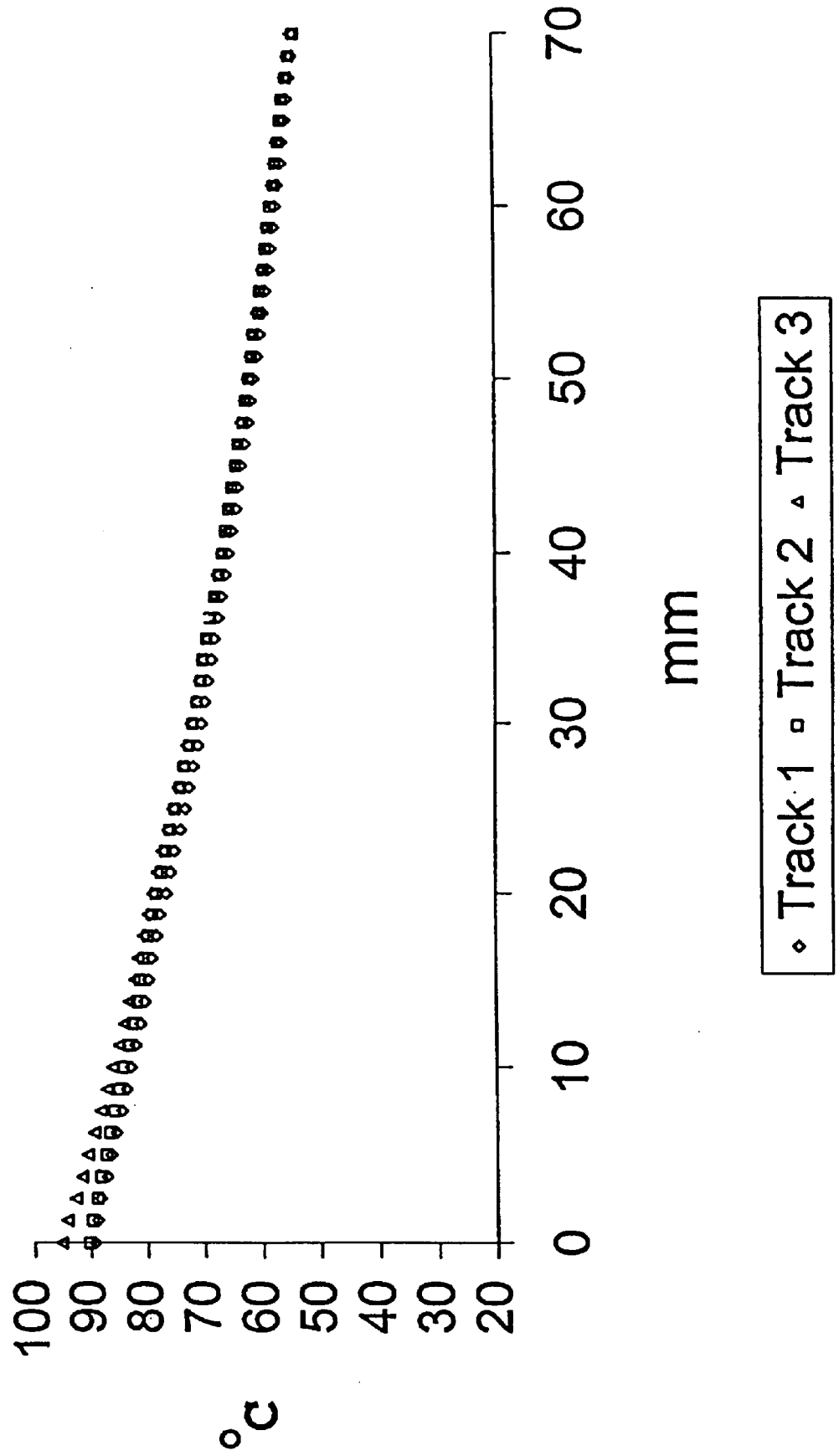
Figure 6C:
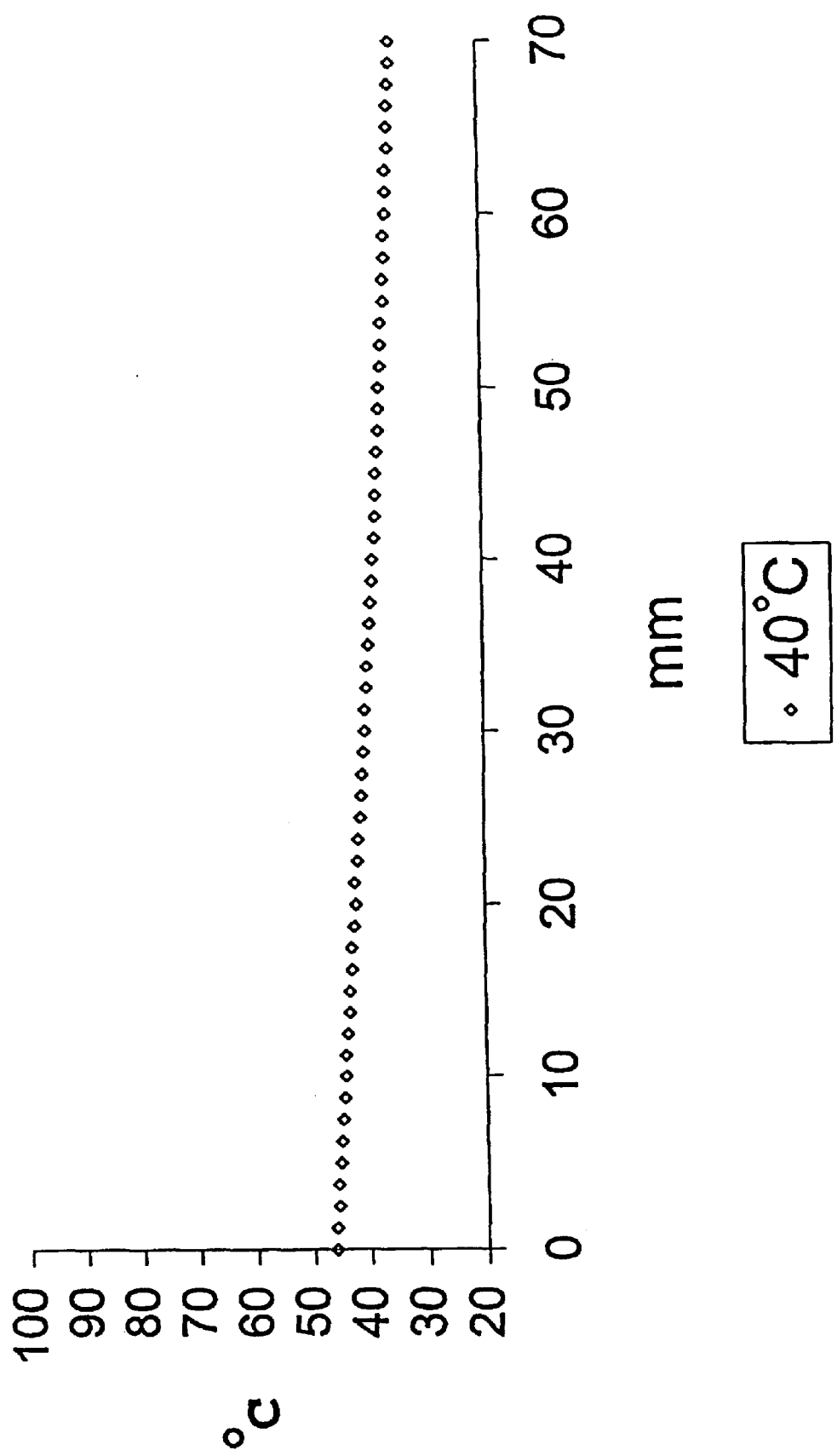
Figure 6D:
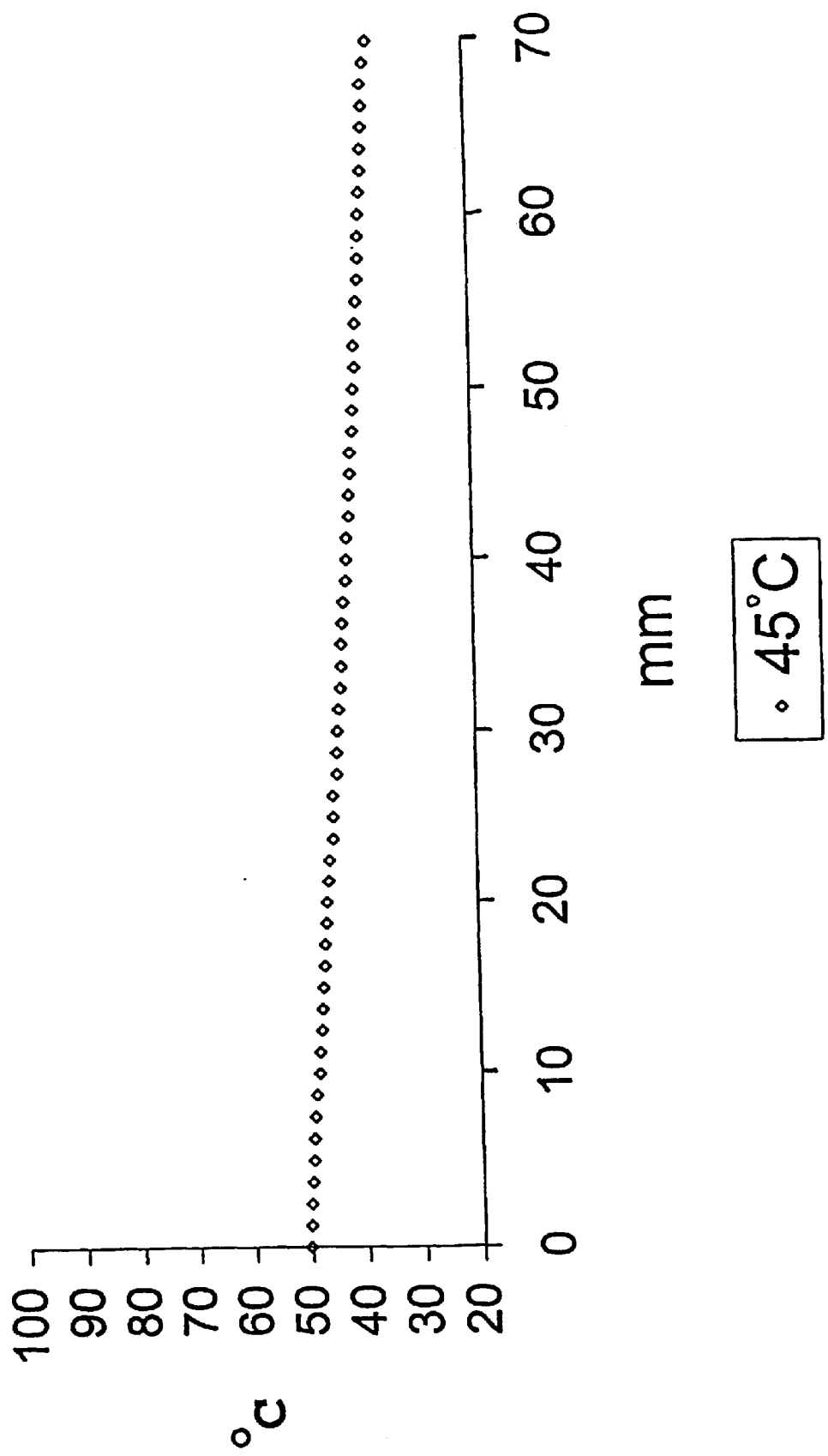
Figure 6F:
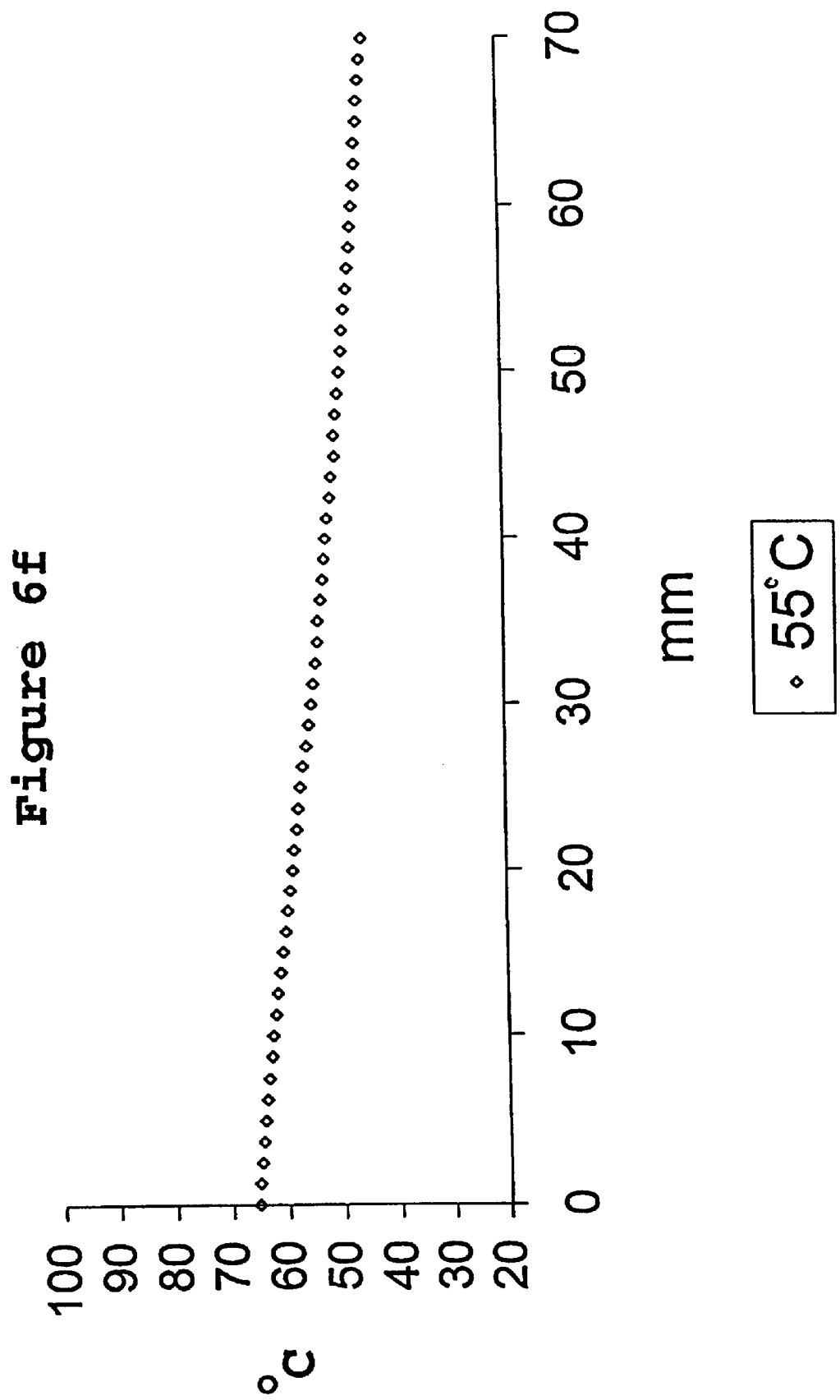
Figure 6G:
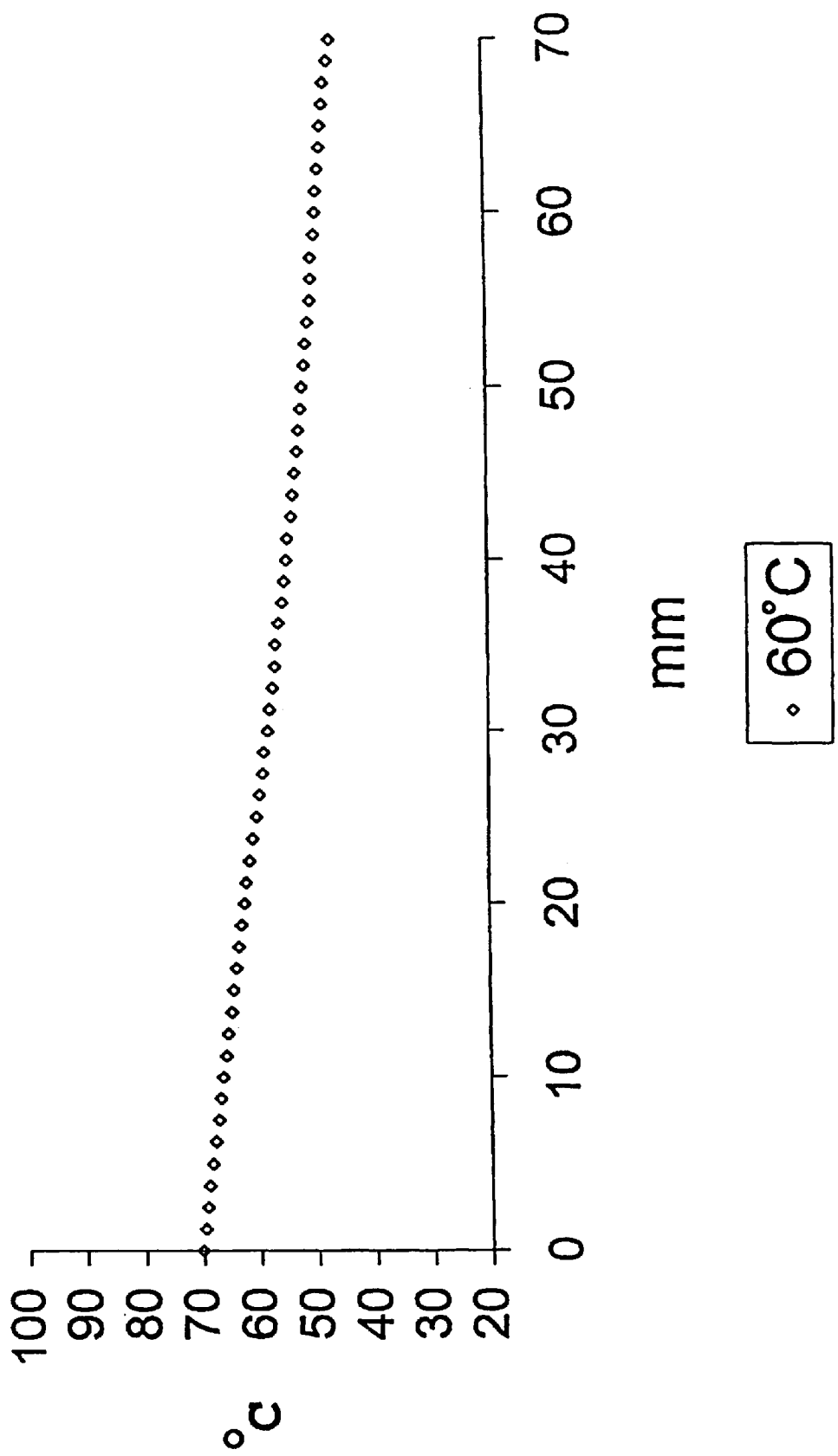
Figure 6H:
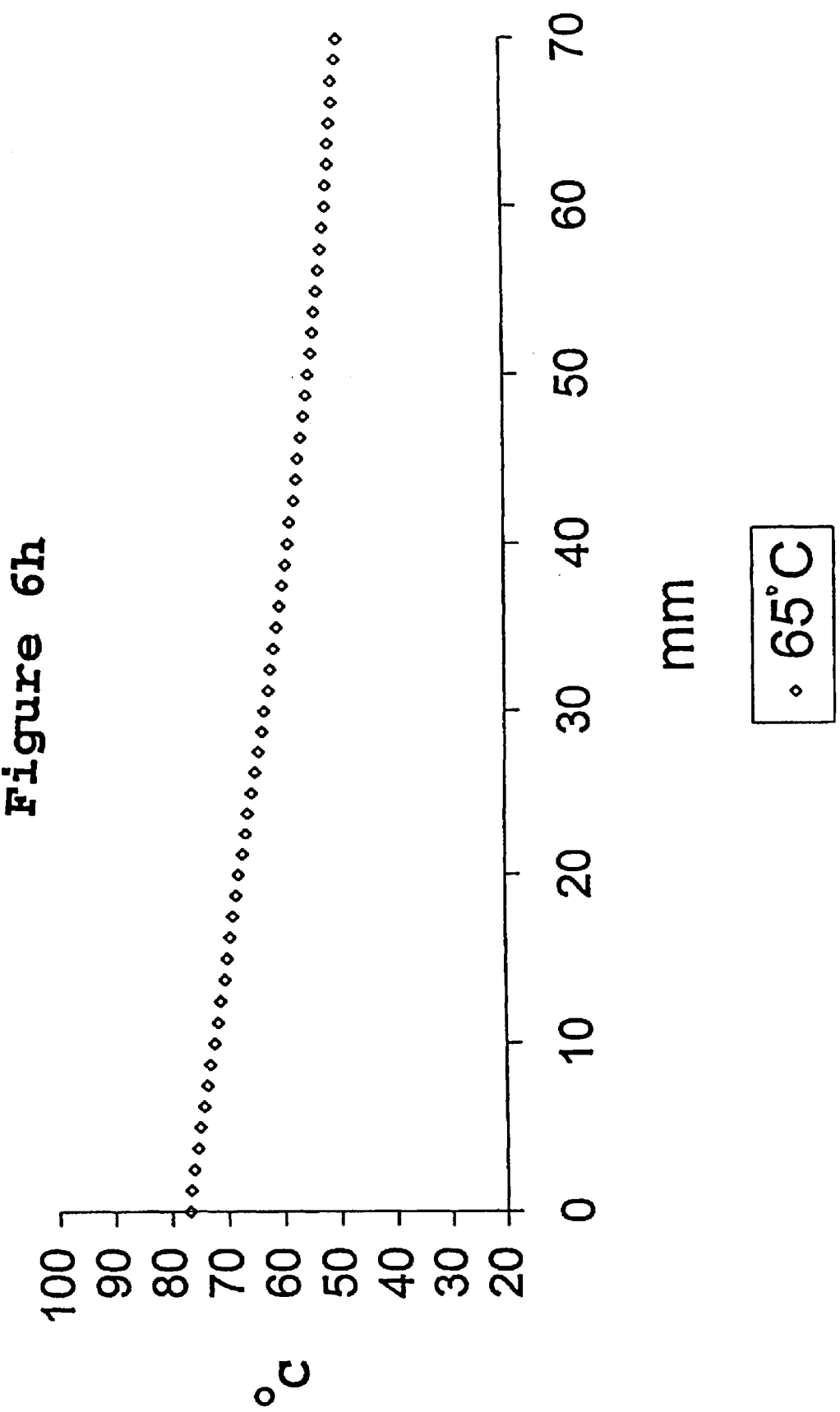
Figure 6I:
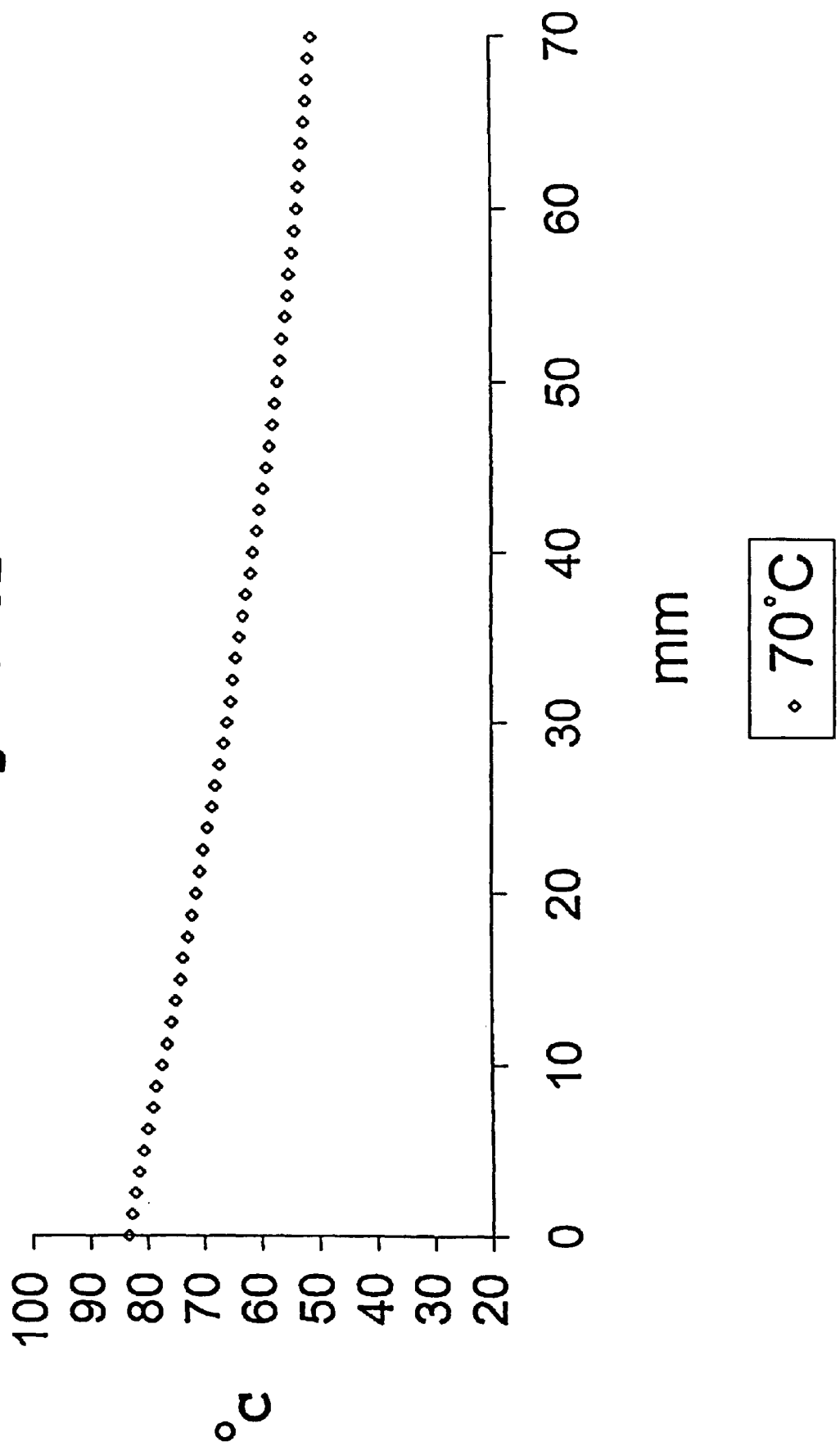
Figure 6J:
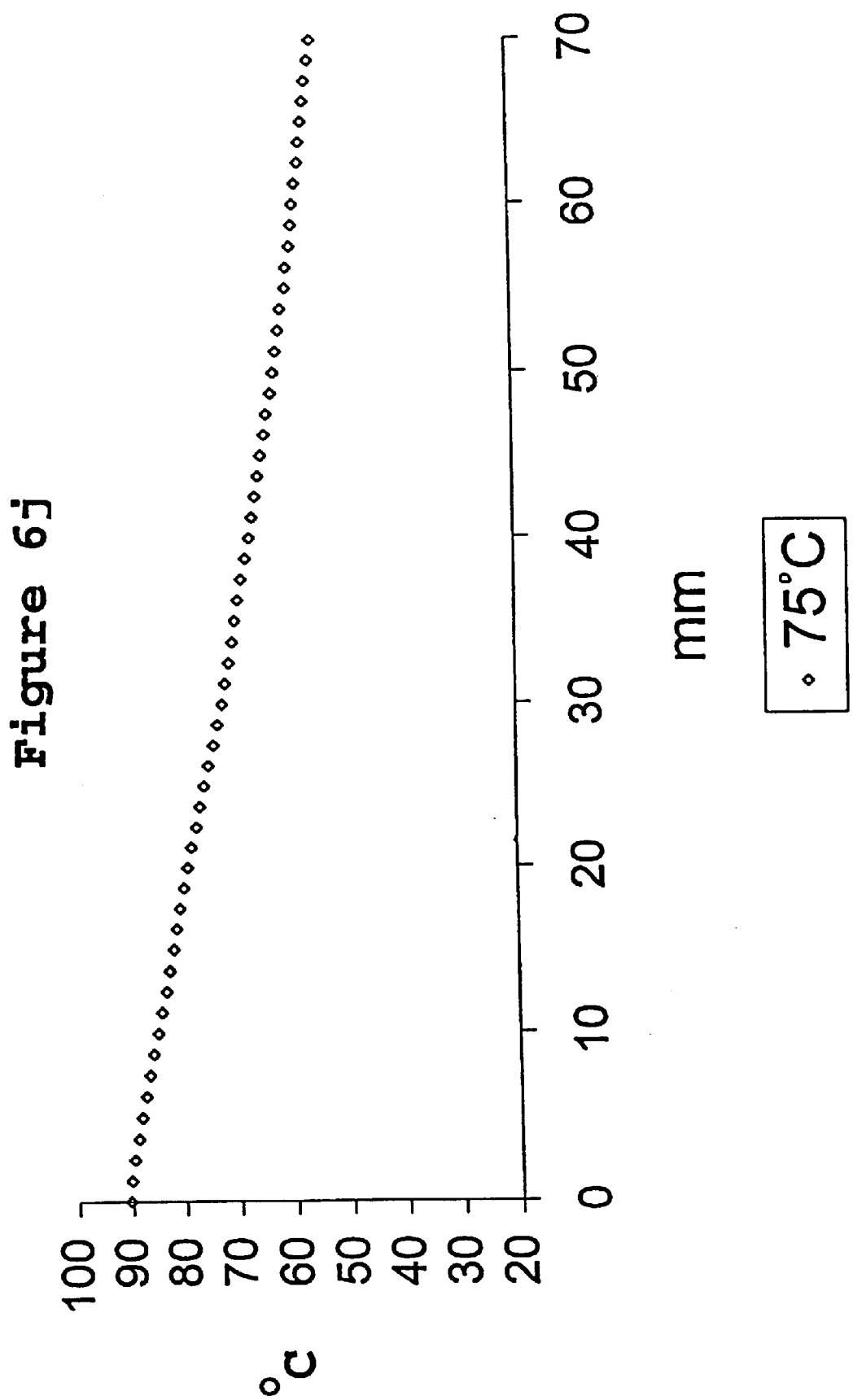
Figure 6K:
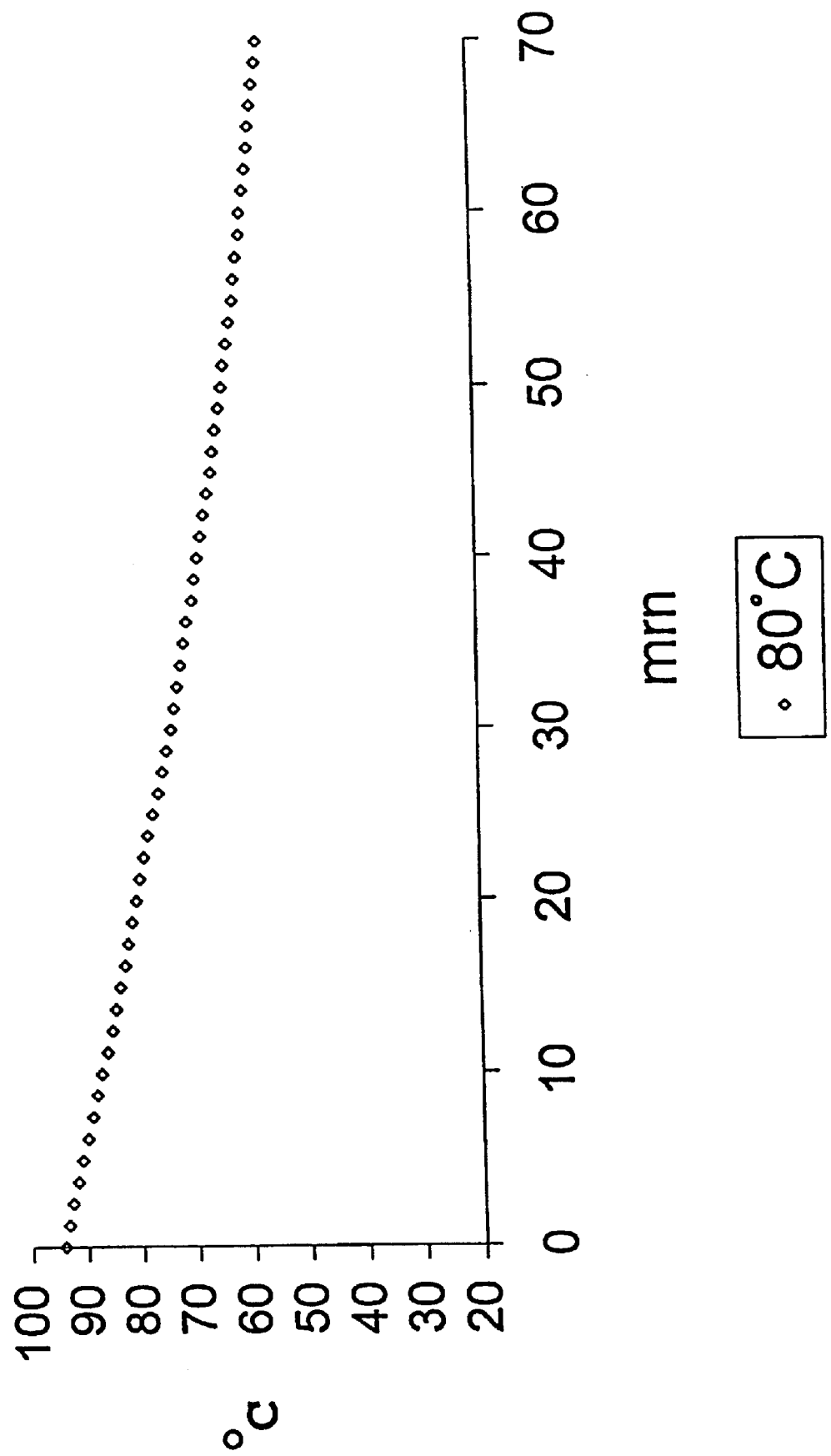

Comparison of the plots in FIG. 6b and FIG. 5c demonstrated that the apparatus of FIG. 6a produced a shallow linear gradient extending across the entire microscope slide, while thermal conductivity alone produced a steep exponential gradient that essentially ended within 20 mm of the source of power.

Example 3

Generation of Different Gradients on a Glass Slide

This example demonstrates generation of different gradient ranges on a glass slide.

The temperature gradient produced by resistive heating and thermal conductivity was generated as described in example 2, and the temperature gradient was visualized as described in example 1. To obtain different temperature gradients, the temperature controller was set to 40° C., 45° C., 50° C., 55° C., 60° C., 65° C., 70° C., 75° C. or 80° C., respectively.

FIG. 6a shows three parallel tracks on the surface of the glass slide, each separated by about 5 mm. The temperature versus position plot along track 1 at each of the set point temperatures is shown in FIG. 6c-FIG. 6k. These results demonstrate that the invention can produce gradients with slopes between 0.1° C./mm and 0.5° C./mm. The slope of the gradient is determined by the set point temperature. Thus, set points of 40° C., 70° C., and 80° C. generate, respectively, gradients with slopes of 0.1° C./mm, 0.3° C./mm and 0.5° C./mm.

Example 4

Gradient on a Glass Microscope Coverslip

This example illustrates the generation of temperature gradients on the surface of glass coverslips placed on a glass microscopic slide with a drop of water. The assembly with the glass slide and the coverslips were placed on a wafer having a temperature gradient.

The gradient apparatus as shown in FIG. 7a was used and the temperature gradient was visualized as described in example 1. A drop of water was placed on top of 3 glass slides. A glass microscope coverslip was placed on each drop of water. Each coverslip had dimensions of about 22 mm×50 mm×0.1 mm. FIG. 7a shows the apparatus with the microscopic glass slides and the coverslips. FIG. 7a also shows a parallel track on each coverslip that was analyzed as described in Example 1. FIG. 7b is a plot of temperature versus position of the three parallel tracks shown in FIG. 7a. As shown in FIG. 7b, a temperature gradient can be formed and maintained on the surface of the coverslip. The temperature gradient formed on the surface of the coverslip was about 0.3° C./mm.

Example 5

Generation of a Gradient on the Surface of a Fluidic Cell

This example illustrates the generation of a gradient on the surface of a fluidic cell containing a glass microscopic slide with DNA.

The resistive heating and thermal conductivity gradient was generated as in example 1. The fluidic cell illustrated in FIG. 8b was positioned on the wafer of the invention as illustrated in FIG. 8a. Temperature on the surface of the top plastic cover of the fluidic cell was visualized as described in example 1.

Figure 8C:
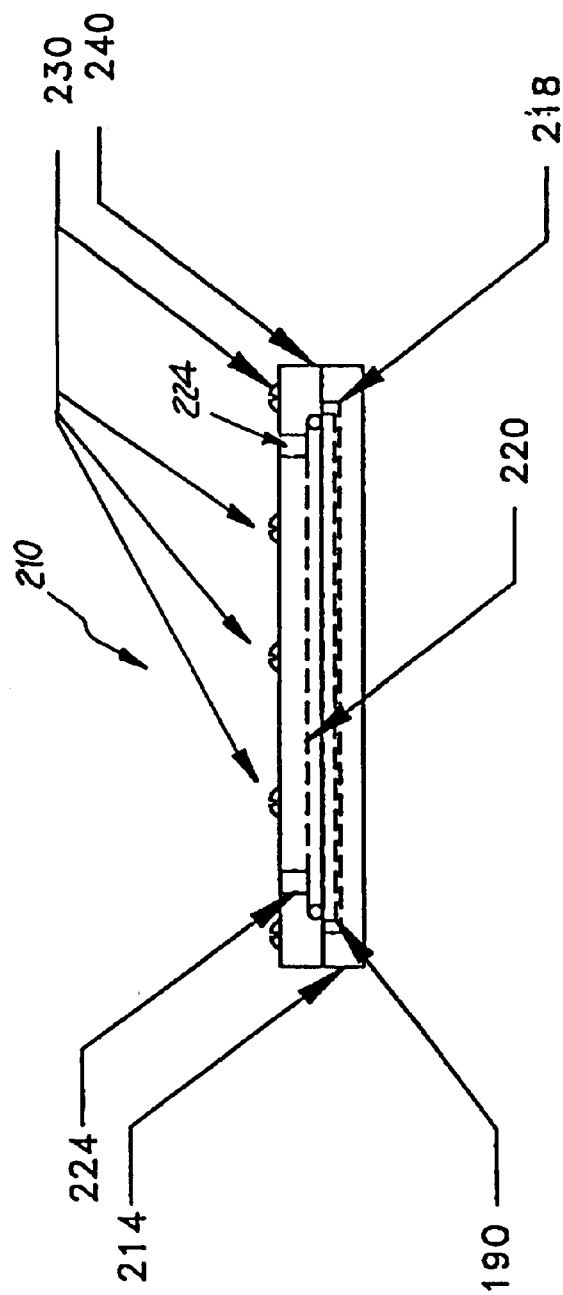
FIG. 8c is a side view of the fluidic cell shown in FIG. 8b.

FIG. 8a shows three parallel tracks on the surface of the fluidic cell, each separated by 5 mm. The temperature versus position plot along these tracks, shown in FIG. 8c, produced three lines that were essentially linear, with slopes of approximately 0.3° C./mm. Therefore, the temperature gradient of the invention can be transferred successively through the lucite base of the fluidic cell, a glass slide, the fluid film covering the glass slide and the lucite lid of the fluidic cell.

Example 6

Generation of a Gradient Along the Length of an Acrylamide Gel

This example illustrates the generation along the length of an acrylamide gel with a gradient apparatus of the present invention.

The resistive heating and thermal conductivity gradient was generated as in example 1. A 5% acrylamide gel was formed between two glass slides as illustrated in FIG. 9b and placed on the wafer of the invention as illustrated in FIG. 9a. Temperature on the surface of the top glass cover of the slide was visualized as described in example 1.

FIG. 9a shows three parallel tracks on the surface of the upper glass slide of the acrylamide gel, each separated by about 5 mm. The temperature versus position plot along these tracks, shown in FIG. 9c, produced three lines that were essentially linear, with slopes of about 0.3° C./mm. Therefore, the temperature gradient of the invention can be transferred successively through a glass slide, an acrylamide gel and another glass slide.

Although the present invention has been described with reference to preferred embodiments, workers skilled in the art will recognize that changes may be made in form and detail without departing from the spirit and scope of the invention.

What is claimed is:

1. A method of generating a temperature gradient comprising: attaching two electrical connectors to a semiconducting wafer, wherein each of the connectors are adjacent to each other and attached to the wafer at an attachment site with a gap disposed between the attachment sites; and connecting a power source to the wafer through the two electric connectors to cause current flow through the wafer and a continuous temperature gradient to be formed on a surface of the wafer.

2. The method of claim 1 wherein the apparatus further comprises a temperature sensor attached to the wafer at the same edge of the wafer to which the electrical connectors are attached and the temperature sensor also being electrically connected to a temperature controller.

3. The method of claim 2 further comprising selecting a set point temperature on the temperature controller.

4. The method of claim 1 wherein the temperature gradient formed is substantially perpendicular to an attachment line connecting the two connectors.

5. The method of claim 4 wherein the temperature gradient formed is between about 0.1° C. per millimeter and about 1.0° C. per millimeter.

6. The method of claim 4 wherein the temperature gradient is between about 0.25° C. per millimeter and about 0.7° C. per millimeter.

7. The method of claim 1 wherein the wafer comprises silicon.

8. The method of claim 1 further comprising placing one or more stratum on the wafer to generate a temperature gradient on the stratum.

9. The method of claim 8 wherein the stratum comprises a material having a thermal conductivity that is significantly lower than that of the surface of the wafer.

10. The method of claim 8 wherein the stratum are selected from the group consisting of microscopic glass slides, fluidic cells, liquid, cover slips, acrylamide gel, DNA chips, protein chips and combinations thereof.

11. A method of generating a temperature gradient on a stratum comprising placing the stratum in thermal contact on a surface having a temperature gradient, the stratum having a thermal conductivity that is significantly lower than that of the surface.

12. The method of claim 11 wherein the surface is a silicon wafer.

13. The method of claim 11 wherein the surface comprises aluminum blocks.

14. The method of claim 11 wherein the temperature gradient on the surface is generated by thermoelectric Peltier devices.

15. The method of claim 11 wherein the stratum comprises materials selected from the group consisting of glass, silicon and plastic.

16. The method of claim 11 wherein the thermal conductivity of the stratum is about 1 W/m/K or less.

17. A method of generating a temperature gradient on a stratum comprising placing the stratum in thermal contact on a surface having a temperature gradient, the stratum comprising materials selected from the group consisting of glass, silicon and plastic.

18. The method of claim 17 wherein the stratum has a thermal conductivity that is significantly lower than that of the surface.

19. The method of claim 18 wherein the thermal conductivity of the stratum is about 1 W/m/K or less.

* * * * *